(12) United States Patent
Amar et al.

(10) Patent No.: US 8,329,643 B2
(45) Date of Patent: Dec. 11, 2012

(54) PIMAP39 MODULATES LPS-INDUCED INFLAMMATORY RESPONSE

(75) Inventors: Salomon Amar, Brookline, MA (US); Xiaoren Tang, Winchester, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 13/000,545

(22) PCT Filed: Jun. 24, 2009

(86) PCT No.: PCT/US2009/048470
§ 371 (c)(1),
(2), (4) Date: Aug. 10, 2011

(87) PCT Pub. No.: WO2009/158409
PCT Pub. Date: Dec. 30, 2009

(65) Prior Publication Data
US 2011/0288035 A1    Nov. 24, 2011

Related U.S. Application Data

(60) Provisional application No. 61/076,076, filed on Jun. 26, 2008.

(51) Int. Cl.
*A61P 29/00* (2006.01)
*A61P 31/00* (2006.01)
*C12N 15/63* (2006.01)
*C07H 21/04* (2006.01)

(52) U.S. Cl. .................... 514/2.1; 435/320.1; 514/12.2; 514/921; 530/324; 536/23.5

(58) Field of Classification Search .................... None
See application file for complete search history.

(56) References Cited

U.S. PATENT DOCUMENTS

2011/0288035 A1* 11/2011 Amar et al. .................. 514/21.3

OTHER PUBLICATIONS

Tang et al (2010. J Innate Immun. 2: 43-55).*
Guha et al, 2001. Cellular Signalling. 13: 85-94).*
Tang, X, et al., (2003) Identification and functional characterization of a novel binding site on TNF-alpha promoter. Proc Natl Acad Sci U S A 100:4096-4101.
Tang, X, et al., (2005) LPS induces the interaction of a transcription factor, LPS-induced TNF-alpha factor, and STAT6 (B) with effects on multiple cytokines. Proc Natl Acad Sci U S A. 102:5132-5137.
Tang, X, et al., (2006) LPS-induced TNF-alpha factor (LITAF)-deficient mice express reduced LPS-induced cytokine: Evidence for LITAF-dependent LPS signaling pathways. Proc Natl Acad Sci U S A 103:13777-13782.
Baeza-Raja, B and Munoz-Canoves, P (2004) p38 MAPK-induced nuclear factor-kappaB activity is required for skeletal muscle differentiation: role of interleukin-6. Mol Biol Cell 15:2013-2026.
Mizuno, T, et al., (2004) The *Caenorhabditis elegans* MAPK phosphatase VHP-1 mediates a novel JNK-like signaling pathway in stress response. Embo J 23:2226-2234.
Tanoue, T, et al., (2000) A conserved docking motif in MAP kinases common to substrates, activators and regulators. Nat Cell Biol 2:110-116.
Chiarugi, P, et al., (2002) Insight into the role of low molecular weight phosphotyrosine phosphatase (LMW¬ PTP) on platelet-derived growth factor receptor (PDGF-r) signaling. LMW-PTP controls PDGF-r kinase activity through TYR-857 dephosphorylation. J Biol Chem 277:37331-37338.
Zatelli, MC, et al., (2005) SRC homology-2-containing protein tyrosine phosphatase-1 restrains cell proliferation in human medullary thyroid carcinoma. Endocrinology 146:2692-2698.
Bamford, S, et al., (2007) Highly purified lipopolysaccharides from *Burkholderia cepacia* complex clinical isolates induce inflammatory cytokine responses via TLR4-mediated MAPK signaling pathways and activation of NFkappaB. Cell Microbiol 9:532-543.
Chi, H, et al., (2006) Dynamic regulation of pro- and anti-inflammatory cytokines by MAPK phosphatase 1 (MKP-1) in innate immune responses. Proc Natl Acad Sci U S A 103:2274-2279.
Zhang, Y, et al., (2004) Regulation of innate and adaptive immune responses by MAP kinase phosphatase 5. Nature 430:793-797.
Fiordalisi, JJ, et al., (2006) PRL tyrosine phosphatases regulate rho family GTPases to promote invasion and motility. Cancer Res 66:3153-3161.
Zeng, Q, et al., (2000) Prenylation ¬ dependent association of protein-tyrosine phosphatases Prl-1, -2, and -3 with the plasma membrane and the early endosome. J Biol Chem 275:21444-21452.
Saha, S, et al., (2001) A phosphatase associated with metastasis of colorectal cancer. Science 294:1343-1346.
Kim, HY, et al., (2003) Curcumin suppresses Janus kinase-STAT inflammatory signaling through activation of Src homology 2 domain-containing tyrosine phosphatase 2 in brain microglia. J Immunol 171:6072-6079.
Mendoza, H, et al., (2008) Roles for TAB1 in regulating the IL-1-dependent phosphorylation of the TAB3 regulatory subunit and activity of the TAK1 complex. Biochem J 409:711-722.
Oliver, FJ, et al., (1999) Resistance to endotoxic shock as a consequence of defective NF-kappaB activation in poly (ADP-ribose) polymerase-1 deficient mice. Embo J 18:4446-4454.
Chvatchko, Y, et al., (2000) A key role for CC chemokine receptor 4 in lipopolysaccharide-induced endotoxic shock. J Exp Med 191:1755-1764.

* cited by examiner

*Primary Examiner* — Zachary Howard
(74) *Attorney, Agent, or Firm* — Pierce Atwood LLP; Kevin M. Farrell; David J. Wilson

(57) ABSTRACT

The present invention relates to a novel peptide sequence named PIMAP39 (herein referred to as SEQ ID NO.: 1) and methods of use of the novel sequence and functional variants thereof. The present invention also relates to methods for reducing and/or modulating inflammatory responses by administration of the peptide of the present invention. Furthermore, the present invention relates to the modulation of the expression of cytokines effected as part of an inflammatory response by administration of the peptide of the present invention.

6 Claims, 14 Drawing Sheets

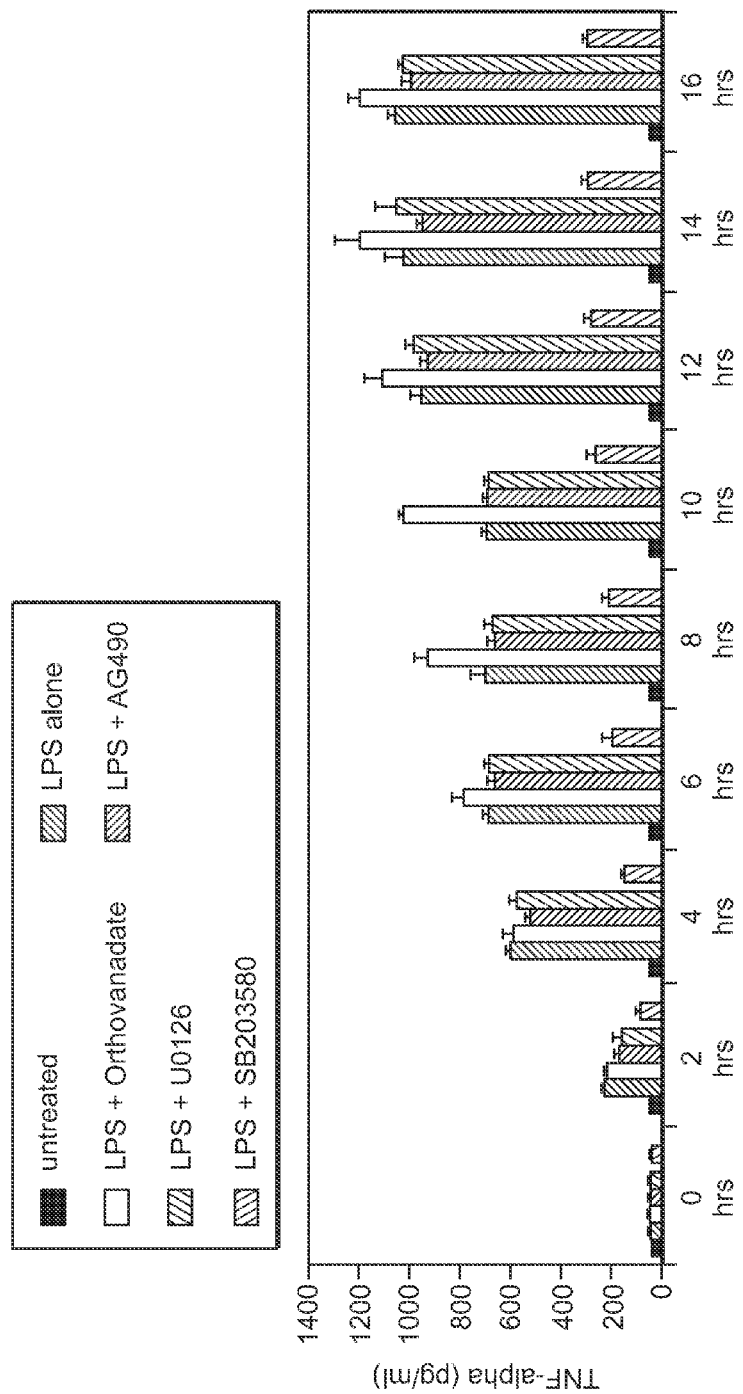

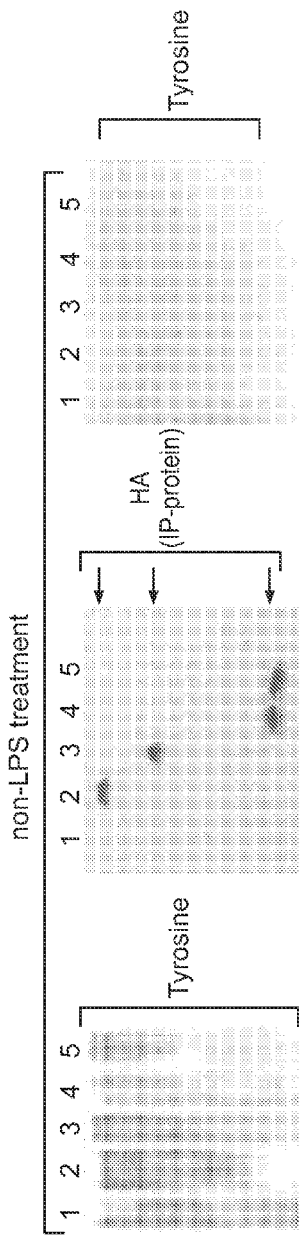
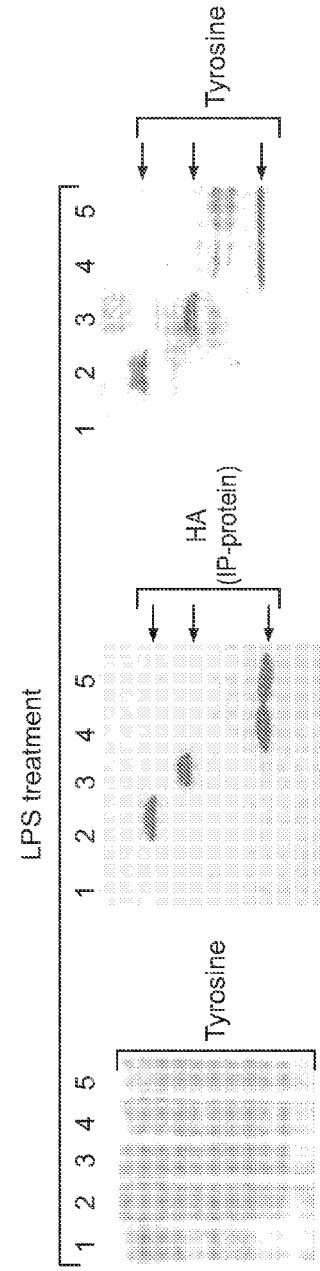

SEQUENCE LISTING

```
<160> NUMBER OF SEQ ID NOS: 16

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Tyr Gly Ala Thr Thr Val Val Arg Val Cys Glu Val Thr Tyr Asp
1               5                   10                  15

Lys Thr Pro Leu Glu Lys Asp Gly Ile Thr Val Val
            20                  25

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atggctcgga tgaaccgc                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctacataacg cagcaccg                                                 18
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atggctcgga tgaaccgccc g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctacataacg cagcaccggg t                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggtgcact gcgtggcggg c                                             21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgaaaacgc cgctggagaa ggat                                          24

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgaagtacg gggctaccac t                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctactgcttg ctgttgatgg c                                             21
```

-continued

```
<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctaacagaac ttggccttca c                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctacacaacg gtgatgccat c                                           21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctacttcagg tcctcaatga a                                           21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctagctcagc cagtcttcca c                                           21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
guacgaggac gccauccagu u                                           21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aacuggaugg cguccucgua c                                           21

<210> SEQ ID NO 16
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Thr Gly Lys Leu Thr Asp Thr Glu Val Val Thr Ala Tyr Val Ile
1               5                   10                  15

Asp Glu Pro Lys Tyr Val Cys Arg Val Thr Gly Lys
            20                  25
```

PIMAP39 MODULATES LPS-INDUCED INFLAMMATORY RESPONSE

This work was supported in part by grant no. DE014079 from the National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Mar. 15, 2012, is named 1462038U.txt and is 4,163 bytes in size.

BACKGROUND

LPS (lipopolysaccharide) is a major integral structural component of the outer membrane of Gram-negative bacteria and activates monocytes and macrophages to produce cytokines such as TNF-α [Young, L R, et al., (2006) Lung-restricted macrophage activation in the pearl mouse model of Hermansky-Pudlak syndrome. J Immunol 176:4361-4368]. LPS stimulates intracellular signaling pathways by regulating activation of cytoplasmic signaling proteins including tyrosine kinases [Zanin-Zhorov, A, et al., (2007) Cutting edge: T cells respond to lipopolysaccharide innately via TLR4 signaling. J Immunol 179:41-44; Khadaroo, R G, et al., (2003) Oxidative stress reprograms lipopolysaccharide signaling via Src kinase-dependent pathway in RAW 264.7 macrophage cell line. J Biol Chem 278:47834-47841] leading to activation of mitogen-activated protein kinase (MAPK), such as p38 MAPK and c-jun-N-terminal kinase (JNK), which is involved in synthesis of certain cytokines [Lin, W N, et al., (2007) Involvement of MAPKs and NF-kappaB in LPS-induced VCAM-1 expression in human tracheal smooth muscle cells. Cell Signal 19:1258-1267; Handley M E, et al., (2005) JNK activation limits dendritic cell maturation in response to reactive oxygen species by the induction of apoptosis. Free Radic Biol Med 38:1637-1652]. The transcription factor (LITAF) that associates with STAT6B and plays a major role in transcription of several inflammatory cytokines including TNF-α [Tang, X, et al., (2005) Identification and functional characterization of a novel binding site on TNF-alpha promoter. Proc Natl Acad Sci USA 100:4096-4101; Tang, X, et al., (2003) LPS induces the interaction of a transcription factor, LPS-induced TNF-alpha factor, and STAT6(B) with effects on multiple cytokines. Proc Natl Acad Sci USA 102: 5132-5137]. Although the mechanism by which it regulates expression of LITAF is not fully investigated, activation of p38 MAPK is required for LITAF gene expression in response to LPS stimulation [Tang, X, et al., (2006) LPS-induced TNF-alpha factor (LITAF)-deficient mice express reduced LPS-induced cytokine: Evidence for LITAF-dependent LPS signaling pathways. Proc Natl Acad Sci USA 103: 13777-13782].

LPS and other compounds are instrumental in inflicting disease and discomfort by stimulating inflammatory reactions. Some such reactions, such as toxic shock syndrome, can be fatal. Although the pathways leading to such outcomes are not totally understood, there is still a need for addressing the treatment of diseases caused by inflammatory responses.

Therefore, what is needed is novel compositions and methods for the treatment of inflammatory diseases.

SUMMARY OF THE INVENTION

The present invention relates to a novel peptide sequence named PIMAP39 (herein referred to as SEQ ID NO: 1) and methods of use of the novel sequence. The present invention also relates to methods for reducing and/or modulating inflammatory responses by administration of the peptide of the present invention. Furthermore, the present invention relates to the modulation of the expression of cytokines effected as part of an inflammatory response by administration of the peptide of the present invention.

In another aspect of the present invention, the peptide of SEQ ID NO: 1 may be modified while still retaining effectiveness in modulating expression of pro-inflammatory cytokines and/or an inflammatory response. In this regard, conservative substitutions may be made to SEQ ID NO: 1 while still retaining functionality of the peptide for the modulation of pro-inflammatory cytokine expression and inflammation. Also, in this regard, amino acids may be added to the 5' and/or the 3' end of the sequence while still retaining functionality of the peptide for the modulation of pro-inflammatory cytokine expression and inflammation, as described below.

In another aspect, the present invention relates to a composition comprising an amino acid sequence consisting of SEQ ID NO: 1, or functional variants thereof. In still another aspect the present invention relates to a composition comprising a nucleotide sequence encoding the amino acid sequence of SEQ ID NO: 1, or functional variants thereof. In still another aspect the present invention relates to an expression vector comprising the nucleotide sequence encoding SEQ ID NO: 1, or functional variants thereof. In another aspect of the invention, any of the above compositions may also comprise a pharmaceutically acceptable carrier.

In another embodiment, it is contemplated that the present invention comprises a method of reducing an inflammatory response in a subject, the method comprising administering to the subject an effective amount of one or more compositions of present invention including, but not limited to, SEQ ID NO: 1, or functional variants thereof. In yet another embodiment of the present invention, it is contemplated that the inflammatory response treated with one or more compositions of the present invention is an LPS-induced inflammatory response.

BRIEF DESCRIPTION OF FIGURES

FIG. 3 shows detection of tyrosine-phosphorylated PTP4A3 and its major deletions in response to LPS stimulation. LPS-untreated (A-C) or treated (D-F) mouse macrophage cells were transiently transfected with non-DNA (lane 1), 1 µg DNAs as described (FIG. 2) of HA-tagged pcHAPTP (lane 2), deletion #2 (lane 3), #7 (lane 4) and #9 (lane 5) using Lipofectamine Reagent. The 30 mg of extract protein from each treated cells was used for Western blot with anti-phosphotyrosine antibody (A & D). The extracts were further purified by immunoprecipitation (IP) with HA (sc-805, Santa Cruz Biotechnology) and their fusion proteins were detected for HA (B & E). After purification, 1 µg IP-proteins of non-LPS-treated (C) or LPS-treated (F) plus non-DNA (lane 1), pcHAPTP (lane 2), deletion #2 (lane 3), #7 (lane 4) or #9 (lane 5) were detected by Western blot with antibodies against 1:4000 dilution of phosphotyrosine (610000, BD Transduction labs).

DETAILED DESCRIPTION OF INVENTION

Figure 1B:
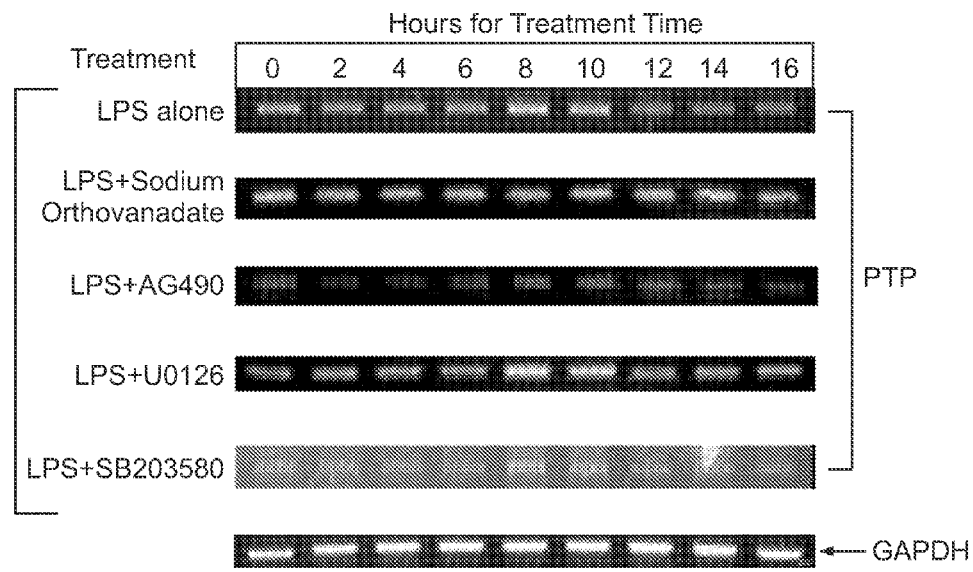
FIG. 1 shows the effects of inhibitors on LPS-induced PTP4A3 production. THP-1 cells were differentiated with 100 nM phorbol-12-myristate-13-acetate (PMA) and seeded ($1 \times 10^5$) in 6-well plates overnight. After washing by PBS, cells were stimulated with 0.1 mg/ml E. coli LPS for 3 hrs. The cells were washed with PBS again and treated with various inhibitors. 10 μM Sodium orthovandate, 20μM AG490, 20μM U0126, 20μM SB203580 or untreated as control. 200μl of supernatant was collected for ELISA assay (A) from each treatment at 2, 4, 6, 8, 12, 14 and 16 hours and its corresponding mRNA was prepared for RT-PCR (B) by first extracting total RNA from the treated cells using QIAQuick™ RNA miniprep (Qiagen). 1μg of each RNA was used to generate cDNA with Platinum® Quantitative RT-PCR ThermoScript™ One-Step System kit (Invitrogen). 10 ng pf cDNA from each test was PCRed using PTP4A3 forward primer 5'-ATGGCTCGGATGAACCGC-3' [SEQ ID NO: 2] and reverse primer 5'-CTACATAACGCAGCACCG-3' [SEQ ID NO: 3]. Another 1 ng of cDNA was PCRed using GAPDH primer pairs (Invitrogen) as control. Densitometric analysis (C) of RT-PCR (B) with intensity values normalized to GAPDH and using 0 hour value as reference intensity.

The present invention relates to a novel peptide that is involved in the regulation of LPS-induced TNF production and modulation of inflammatory responses as well as compositions derived from the novel peptide and methods for the use of such compositions in modulating cytokine expression in a cell and the inflammatory response in an organism. The present invention is based in part on the identification of a novel peptide (KYGATTVVRVCEVTYDKTPLEKDG-ITVV [SEQ ID NO: 1]) herein called PIMAP39. Although the present invention is not limited to any particular theory, the novel sequence of the present invention (and derivatives of the sequence) is believed to suppress LITAF/TNF production in response to, for example, LPS stimulation. Additionally, the invention provides the use of SEQ ID NO: 1 for modulating the expression of genes other than LITAF or TNF and for the modulation, inhibition or reduction of LPS-induced immune reactions.

The present invention also relates to the introduction of the PIMAP39 peptide of the present invention into a cell or cells in vitro or in vivo. The novel sequence of the present invention [SEQ ID NO: 1], or derivatives thereof, may be introduced into a cell or cells by any of the methods known in the art. Methods of introducing proteins into a cell or cells are well known in the art and are provided in detail in, for example, Sambrook, J., Fritsch, E. F. and Maniatis, T., Molecular Cloning: A Laboratory Manual. Cold Spring Harbor Laboratory Press, NY, Vol. 1, 2, 3 (1989), which is incorporated herein by reference. In brief, proteins may be introduced into cells in two general ways. The first is with the transfection of nucleic acids expressing the desired protein. Once inside the cell the protein is produced by the cell's own transcription and translation components. The second is with the transfection of the actual protein into the cell.

The transfection of nucleic acids is well known in the art. The nucleic acid sequence (for example, the nucleic acid sequences of the present invention) encoding the desired protein is operably inserted into an expression vector suitable for the transcription and translation of the nucleic acid sequence into the desired protein. A large number of expression vectors are commercially available (e.g., pCAT, Promega, Madison, Wis.; pBlueScript and pCMV, Stratagene, La Jolla, Calif.). The splicing of a specific nucleotide sequence into an expression vector is also well know in the art as is referenced above in Sambrook, et al. Suitable transfection methods include DEAE-dextran, calcium phosphate precipitation, Lipofectamine™ (Invitrogen, Carlsbad, Calif.), Profectin™ (Promega, Madison, Wis.) and other liposome methods, direct microinjection, electroporation and bioloastic particle delivery, for example. Any primary cell type or any cell line may be used for the present invention. The PIMAP39 peptide of the present invention may also have additional amino acids added to either of the amino or carboxy terminals. Anywhere form zero to 100 or more amino acids may be added to one or both peptide terminals. Examples of sequences to be added may be, for example, tags for the detection of or for determining the location(s) of the peptide within the cell. Amino acid sequences for tethering the PIMAP39 peptide of the present invention to a specific location in a cell or tissue or to a specific surface (e.g., the surface in a reaction vessel). Non-limiting examples of suitable tethering sequences include the lambda bacteriophage antiterminator protein N (lambdaN-(1-22) or lambdaN peptide) (J. Baron-Benhamou, et al., Methods Mol. Biol., 257:135-154, 2004, which is herein incorporated by reference), a glycine-serine tether (U.S. Pat. No. 7,074,557, which is herein incorporated by reference). Or, sequences for aiding in the transport of the peptide through, for example, cell or organelle membranes or for transport through selective pores in organelle or cell membranes. Many tags, tethering sequences and sequences to aid in transport into and through cells or organelles are well known to those practiced in the art.

Transfection of the actual peptides of the present invention (i.e., proteins comprising [SEQ ID NO: 1]) may take place by, for example, transport (active or passive) or by microinjection. Active transport is a process whereby cells absorb material from the outside the cell by engulfing it with the cell membrane. Passive transport may also take place via the passage of peptide fragments, for example, into the cell through pores. Cells frequently transport particles and, especially, proteins and protein fragments into the cell's cytoplasm. Transport may be specific via, for example, specific receptors or it may be more general. With general forms of active transport the cell engulfs constituents from the extracellular milieu. This is often referred to as pinocytosis. Pinocytosis (literally, cell-drinking) is the invagination of the cell membrane to form a pocket filled with extracellular fluid (and molecules within it). The pocket then pinches off to form a vesicle, and the vesicle ruptures to release its contents into the cytoplasm.

In addition to the techniques given directly above, transfection of the proteins of the present invention into cells may also be executed by the transfection of nucleic acids that express the peptide(s) of the present invention into cells, as given above. Any primary cell type or any cell line may be used as a recipient for the peptides and nucleic acid sequences of the present invention. The techniques of nucleic acid transfection are well known in the art (see, for example, Sambrook, et al., herein incorporated by reference).

Peptides comprising, consisting essentially of or consisting of SEQ ID NO: 1 also have the ability to modulate cytokine expression in the methods of the present invention (see, Examples). A biologically active peptide may further be a protein, polypeptide or peptide. As defined in this invention, the terms "protein," "peptide" or "polypeptide" are interchangeable and refer to a sequence of two of more amino acids with or without additional modifications such as, but not limited to, glycosylation.

The present invention also relates to methods for the modulation of cytokine expression, especially of TNF-α and any other associated inflammatory cytokines. These may include, for example, introducing into a cytokine-responsive cell a composition comprising SEQ ID NO: 1. In this method, SEQ ID NO: 1 is to be introduced into the cell in an amount effective to modulate cytokine expression. Amounts may vary depending on, for example, the target cell or tissue type but can be determined easily via titration of the peptide or expression construct used. The cytokine to be modulated may be, for example, TNF-α and/or IL-1β or other cytokine associated with an inflammatory response. Introduction of [SEQ ID NO: 1] into the cell decreases expression of, for example, TNF-α, and, as such, this method may be used to effect any of the cellular processes resulting from the same.

One of skill in the art will recognize that a biologically active peptide comprising [SEQ ID NO: 1] may be used in lieu of the peptide of the present invention. A "biologically active peptide" is intended to encompass any mimetic, truncation, deletion and/or substitution or elongation of the peptide sequence of the present invention. In one embodiment, the peptide of SEQ ID NO: 1 comprises an additional 0-100 amino acids in sequence with one or both of the amino- or carboxy-terminals of the peptide.

One of skill in the art will recognize that the peptide of [SEQ ID NO: 1] or proteins comprising the active peptide of [SEQ ID NO: 1] may be introduced into a cell by various means in the methods of the present invention. A cell may be contacted directly with the peptide of [SEQ ID NO: 1] or proteins comprising active of [SEQ ID NO: 1] under conditions for cellular uptake. Such conditions include but are not limited to injection and calcium chloride mediated uptake, electroporation, microinjection, etc. Alternatively, a target cell (e.g., a cytokine-responsive cell) may express exogenous [SEQ ID NO: 1] or proteins comprising active [SEQ ID NO: 1] from an introduced exogenous construct harboring an expressible cDNA construct or constructs, as discussed above.

In the methods of the present invention, a composition comprising [SEQ ID NO: 1] or proteins comprising [SEQ ID NO: 1] may be administered to an animal or individual in a physiologically acceptable carrier in a therapeutically effective amount. Said compound or compounds may be administered alone or in combination with other therapies and may be delivered intravenously, subcutaneously or orally to an animal. Administration may be systemic although local administration may be preferable.

It is an object of the present invention to employ the methods disclosed herein for modulating cellular responses to cytokine expression. The methods of the present invention may be used to study and/or treat diseases associated with aberrant cytokine signaling. It is known in the art that cytokine signaling is involved in pro-inflammatory and anti-inflammatory responses to pathogens and in cellular proliferation and differentiation in a variety of cells. Thus, methods disclosed herein for modulating cytokine signaling may be used to alter these and other cytokine-dependent processes in normal and/or abnormal cells.

TNF-alpha (tumor necrosis factor-alpha; TNF-α) is a cytokine released by, for example, white blood cells in the course of damage by, for example, infection. Unregulated release of TNF-alpha has been implemented in the etiology of several diseases including, for example, various autoimmune disorders such as rheumatoid arthritis, Crohn's disease and psoriasis.

Interleukin-1-beta, (IL-1-beta) is a cytokine implemented in numerous diseases including acute phase response (the near immediate response by the immune system in injury that is typically characterized by, e.g., redness and swelling). It is secreted by macrophages, monocytes and dendritic cells. The secretion of both TNF-alpha and IL-1-beta are regulated by LITAF expression. Thus, the inhibition of LITAF expression by, for example, SEQ ID NO: 1 can be used to modulate the secretion of both these cytokines since decreases in LITAF expression leads to decreases in both TNF-alpha and II-1-beta expression.

Thus, the modulation of cytokine signaling via the compositions and methods of the present invention may also be used to modulate the immune response of an animal or individual to an antigen, or to treat diseases or repair of damage caused by such as, for example, inflammatory diseases or diseases with inflammation as part of their etiology.

Although the present invention is not limited by theory, it is believed by the Inventors of the present invention that LPS stimulation of macrophages initiates intracellular signaling pathways leading to activation of mitogen-activated protein kinase (MAPK) and its subsequent influence in cytokine production. The Inventors recently identified a LITAF-STAT6 (B) complex that translocated into the nucleus, where it significantly regulated TNF-α. (See, co-pending U.S. Provisional Patent Application No. 60/838,217 (also, published as WO2008/021160), which is incorporated herein by reference). Also, it is known that p38 MAPK specifically activates LITAF gene expression and PTP4A3 inhibits LITAF promoter activity in response to LPS stimulation. However, the LPS-induced cascade in the p38/LITAF/TNF signaling pathway remains unclear in the art. In this invention it is shown that PTP4A3 [e.g., GenBank Accession No. AAH66043, murine; BC003105, human], a protein tyrosine phosphatase, is a novel negative regulator of LPS-induced LITAF/TNF-α production. In is believed that PTP4A3 elicits its negative role by selectively dephosphorylating p38αMAPK in response to LPS stimulation of macrophages. PTP4A3 expression is up-regulated in macrophages and undergoes tyrosine phosphorylation in LPS-dependent manner. Further structure-function analysis revealed that a novel short peptide (PIMAP39; [SEQ ID NO: 1]) derived from PTP4A3 is capable of mimicking the functionality of full-length PTP4A3 to dephosphorylate p38α and suppress LPS-induced LITAF/TNF-α production. Treatment of mice with PIMAP39 significantly attenuates the severity of adverse host responses to LPS stimulation, and in some cases provides resistance to a lethal dose of LPS due to suppression of TNF-α production. All together, these results reveal a previously unrecognized and unpredicted role for PTP4A3 in LPS signaling and pave the way for pharmacological interventions using PIMAP39 in inflammatory conditions.

In the Inventor's recent U.S. provisional application (60/838,217; WO2008/021160), a transcription factor was identified (LITAF) that interacts with STAT6(B) and forms a stable complex in the cytoplasm in response to LPS. The translocation of LITAF-STAT6(B) complex into the nucleus, significantly regulates transcription of several inflammatory cytokines including TNF-α [Tang, X, et al., (2005) Identification and functional characterization of a novel binding site on TNF-alpha promoter. Proc Natl Acad Sci USA 100:4096-4101; Tang, X, et al., (2003) LPS induces the interaction of a transcription factor, LPS-induced TNF-alpha factor, and STAT6(B) with effects on multiple cytokines. Proc Natl Acad Sci USA. 102:5132-5137]. LPS mediated p38 MAPK activation serves as an upstream kinase of LITAF which specifically activates LITAF gene expression [Tang, X, et al., (2006) LPS-induced TNF-alpha factor (LITAF)-deficient mice express reduced LPS-induced cytokine: Evidence for LITAF-dependent LPS signaling pathways. Proc Natl Acad Sci USA 103:13777-13782].

p38 MAPK is activated by various growth factors and cytokines and its activity is suppressed by protein tyrosine phosphatases [Baeza-Raja, B and Munoz-Canoves, P (2004) p38 MAPK-induced nuclear factor-kappaB activity is required for skeletal muscle differentiation: role of interleukin-6. Mol Biol Cell 15:2013-2026; Mizuno, T, et al., (2004) The *Caenorhabditis elegans* MAPK phosphatase VHP-1 mediates a novel JNK-like signaling pathway in stress response. Embo J 23:2226-2234; Tanoue, T, et al., (2000) A conserved docking motif in MAP kinases common to substrates, activators and regulators. Nat Cell Biol 2:110-116; Chiarugi, P, et al., (2002) Insight into the role of low molecular weight phosphotyrosine phosphatase (LMWPTP) on platelet-derived growth factor receptor (PDGF-r) signaling. LMWPTP controls PDGF-r kinase activity through TYR-857 dephosphorylation. J Biol Chem 277:37331-37338]. In the human MTC cell line TT, SRIF stimulated the PTP activity which is associated with inhibition of proliferation and reduced MAPK activity. Blockade of PTP activity with sodium orthovanadate has been shown to induce cell proliferation and increased p38 MAPK phosphorylation [Zatelli, M C, et al., (2005) SRC homology-2-containing protein tyrosine phosphatase-1 restrains cell proliferation in human medullary thyroid carcinoma. Endocrinology 146:2692-2698]. Our initial observation indicates that in addition to these effects, PTP activity inhibits LITAF promoter activity (our unpublished data). The current study has identified a possible link between PTP4A3 and LPS-induced p38 MAPK activation and its subsequent influence in LPS-induced cytokine production.

Several studies have indicated that p38 MAPK is activated in differentiating myocytes, where NF-κB activity is present [Bamford, S, et al., (2007) Highly purified lipopolysaccharides from *Burkholderia cepacia* complex clinical isolates induce inflammatory cytokine responses via TLR4-mediated MAPK signaling pathways and activation of NFkappaB. Cell Microbiol 9:532-543], but suppressed by protein tyrosine phosphatases (PTPs). In particular, dual-specificity protein phosphatases are known to play a key role in regulation of p38 MAPK activity [Baeza-Raja, B and Munoz-Canoves, P (2004) p38 MAPK-induced nuclear factor-kappaB activity is required for skeletal muscle differentiation: role of interleukin-6. Mol Biol Cell 15:2013-2026; Mizuno, T, et al., (2004) The *Caenorhabditis elegans* MAPK phosphatase VHP-1 mediates a novel JNK-like signaling pathway in stress response. Embo J 23:2226-2234; Tanoue T, et al., (2000) A conserved docking motif in MAP kinases common to substrates, activators and regulators. Nat Cell Biol 2:110-116]. For instance, DUSP1/MKP-1 inactivates p38 MAPK in mouse macrophages and serves as a negative regulator of a subset of genes in response to LPS [Chi, H, et al., (2006) Dynamic regulation of pro- and anti-inflammatory cytokines by MAPK phosphatase 1 (MKP-1) in innate immune responses. Proc Natl Acad Sci USA 103:2274-2279]. Interestingly, the expression of DUSP10/MKP-5, another member of dual-specificity protein phosphatase, is strongly induced in macrophages exposed to LPS. DUSP10/MKP-5 regulates JNK activation without an apparent effect on p38MAK activation [Zhang, Y, et al., (2004) Regulation of innate and adaptive immune responses by MAP kinase phosphatase 5. Nature 430:793-797]. Altogether, these findings underscore the role of PTPs to significantly modify the biological outcome of LPS-induced pro-inflammatory response in macrophages.

Recently, it was found by the present inventors that PTP4A3, a unique protein tyrosine phosphatase (also called Phosphatase of regenerating liver-3, PRL3), which is modified by farnesylation [Fiordalisi, J J, et al., (2006) PRL tyrosine phosphatases regulate rho family GTPases to promote invasion and motility. Cancer Res 66:3153-3161], inhibits LITAF promoter activity (our unpublished data). PRLs constitute a novel class of small tyrosine phosphatases which includes three members, PRL-1, PRL-2 and PRL-3 [Zeng, Q, et al., (2000) Prenylation dependent association of protein-tyrosine phosphatases PRL-1, -2, and -3 with the plasma membrane and the early endosome. J Biol Chem 275:21444-21452] and recent studies suggest a key role for these PTPs in tumor growth and metastasis [Saha, S, et al., (2001) A phosphatase associated with metastasis of colorectal cancer. Science 294:1343-1346]. In the invention study, the involvement of PTP4A3 in LPS-induced LITAF/TNF-α production has been characterized. Our study indicates that PTP4A3 regulates dephosphorylation of p38αMAPK in THP-1 or macrophage cells in response to LPS stimulation. Furthermore, a specific short peptide of PTP4A3, PIMAP39, is found to mimic the function of the full-length PTP4A3 for its ability to dephosphorylate p38α and to down-regulate LITAF/TNF-α production in response to LPS stimulation. This unique peptide sequence derived from PTP4A3 is highly conserved among species and unexpectedly is cell permeable both in an in vitro cell culture and in vivo systems. Treatment of animals with PIMAP39 peptide decreases the severity of the adverse host responses to LPS stimulation, and in some cases provides complete resistance to an otherwise lethal dose of LPS. All together, these results reveal a novel and previously unrecognized role for PTP4A3 in LPS signaling.

Although the role of PTP4A3 in cancer growth and metastasis is extensively analyzed [Saha, S, et al., (2001) A phosphatase associated with metastasis of colorectal cancer. Science 294:1343-1346], nevertheless the putative function of PTP4A3 in LPS-induced inflammatory responses remains largely unknown. Our present data indicate that although PTP4A3 does not affect the activation of Akt, JAK, ERK or NFKB p65, it selectively dephosphorylates LPS-induced p38αMAPK phosphorylation in both THP-1 and mouse macrophages. The initial observation suggested that PTPs are involved in the regulation of LPS-induced production of TNF-α [Kim, H Y, et al., (2003) Curcumin suppresses Janus kinase-STAT inflammatory signaling through activation of Src homology 2 domain-containing tyrosine phosphatase 2 in brain microglia. J Immunol 171:6072-6079; Mendoza, H, et al., (2008) Roles for TAB1 in regulating the IL-1-dependent phosphorylation of the TAB3 regulatory subunit and activity of the TAK1 complex. Biochem J 409:711-722] but the role of PTP4A3 in this system is poorly known. In this study a specific short peptide (PIMAP39) is found to mimic the activity of full-length PTP4A3 to dephosphorylate p38α and to suppress LITAF/TNF production in response to LPS stimulation. The analysis of PIMAP39 shows that this unique sequence is located upstream of both the catalytic area and SH2 domain. Surprisingly and unexpectedly, PIMAP39 peptide is able to easily penetrate into mouse macrophage cells in vitro and be taken up by mouse white blood cells in vivo, without any cell delivery vehicle such as transfection agents. Indeed, treatment of mice with 40 μg/g of PIMAP39, or even a low concentration (0.4 μg/g), efficiently delays sickness and prolongs survival time by about 4-5 hrs compared to controls most likely due to the peptide efficiently downregulating LPS-induced TNF-α production. In support of its functional role in vivo the analysis of blood samples from mice injected with PIMAP39 shows that these mice maintain a 78.3% lower concentration of TNF-α compared to control mice that typically display a rapid increase in TNF-α production within 6 hrs. The data suggest that mice treated with PIMAP39 significantly resist LPS-induced endotoxic shock most likely due to the suppression of TNF-α production.

Several studies indicated that mice lacking a gene, such as poly (ADP-ribose) polymerase-1 (PARP-1), or a receptor, such as CC chemokine receptor 4 (CCR4), are resistant to LPS-induced death suggesting that these are involved in the regulation of the NF-KB signaling pathway leading to synthesis of inflammatory mediators, and the development of LPS-induced endotoxic shock [Oliver, F J, et al., (1999) Resistance to endotoxic shock as a consequence of defective NF-kappaB activation in poly (ADP-ribose) polymerase-1 deficient mice. Embo J 18:4446-4454; Chvatchko, Y, et al., (2000) A key role for CC chemokine receptor 4 in lipopolysaccharide-induced endotoxic shock. J Exp Med 191:1755-1764]. However, these studies provide only a limited explanation of the role of these factors in LPS-induced endotoxic shock. In this study, treatment with PIMAP39 actually prevented LPS-induced death in 12.5% of the mice suggesting a different mechanism of attenuating adverse host responses to LPS-induced endotoxemia. The specific amino acid residue of PIMAP39 (100% homologous) within a conserved region of multiple groups including mouse, monkey and human was identified, which will enable the present inventors to design additional animal models to further clarify the functional capabilities of PIMAP39 in alleviating the symptoms of LIPS-induced diseases.

Current studies also demonstrate that LPS treatment of monocyte cells increases tyrosine phosphorylation of certain proteins, and that Herbimycin-A and genistein, general inhibitors of tyrosine kinases, markedly attenuated LPS-induced TNF-α expression both at the protein and mRNA levels. The ability of LPS to promote TNF-α production was further enhanced by treatment of cells with tyrosine phosphatase inhibitor, sodium orthovanadate. However, the timing of the LPS-dependent phosphorylation of proteins on tyrosine remains unclear. In the present application it is shown that LPS stimulation induces an accumulation of PTP4A3 between 8-10 hrs, after which its expression immediately decreases and eventually returns to its normal level. During this period, the maximal level of PTP4A3 coincides with no increase in the LPS-induced TNF-α protein rate, suggesting that LPS-induced PTP4A3 is the short-lived protein responsible for temporally inhibiting TNF-α production at this time point. Afterwards, TNF-α production resumes due to the rapid degradation or inactivation of PTP4A3. It was also found, herein, that PTP4A3 is always expressed at a basal level, and while this is a low level for most cells, such as fibroblasts, its basal expression level in THP-1 or macrophage cells is relatively high (our unpublished data). In addition, co-treatment of cells with LPS and orthovanadate augmented the LPS-induced expression of TNF-α (see FIG. 1, 8-16 hrs), suggesting that PTPs play an important role in the fine-tuning of immune response. Altogether, the data demonstrate that without PTP4A3, cells are more sensitive to LPS stimulation, but further work is required to shed new light on the mechanisms involved.

While specific embodiments of the present invention have been described, it will be apparent to those skilled in the art that various modifications thereto can be made without departing from the spirit and scope of the invention as defined in the examples and appended claims.

EXEMPLIFICATION

Materials and Methods

All bacterial cloning constructs used *Escherichia coli* strain DH5a (Invitrogen, Carlsbad, Calif.). U20S human osteosarcoma cells (wt) were grown in DMEM supplemented with 10% fetal bovine serum (FBS). THP-1 cells [TIB-202, American Type Culture Collection (ATCC), Manassas, Va.] were grown in RPMI 1640 supplemented with 10% FBS (fetal bovine serum). All human cell cultures were maintained in a 37° C. humidified atmosphere containing 5% $CO_2$. *E. coli* LPS was purchased from Sigma-Aldrich (Saint Louis, Mo.).

Macrophages

Macrophages were obtained from C57BL/6 mice (The Jackson Laboratory, Bar Harbor, Me.) and purified by conventional methods [Shimomura, H, et al., 2001]). Lipopolysaccharide of *Burkholderia* cepacia and its unique character to stimulate murine macrophages with relative lack of interleukin-1 beta inducing ability. Infect Immun 69:3663-3669].

Mice

All mice (WT) were 8-12 weeks of age and maintained under strict pathogen-free (SPF) conditions at the Boston University transgenic facility. All procedures involving animals were approved by the Institutional Animal Care and Use Committee at Boston University Medical Center.

Kinase Inhibitors

AG490, U0126 and SB203580 were purchased from EMD Biosciences (San Diego, Calif.). Sodium orthovanadate was purchased from Sigma-Aldrich (Saint Louis, Mo.). Human THP-1 cells were treated with 10 μM Sodium orthovanadate (PTP4A3 inhibitor [Greenwel, P, et al., (1995) Tyrosine dephosphorylation of nuclear proteins mimics transforming growth factor beta 1 stimulation of alpha 2(1) collagen gene expression. Mol Cell Biol 15:6813-6819], 20 μM AG490 (JAK inhibitor [Saudemont, A, et al., (2007) Dormant tumor cells develop cross-resistance to apoptosis induced by CTLs or imatinib mesylate via methylation of suppressor of cytokine signaling 1. Cancer Res 67:4491-4498], 20 μM U0126 (ERK inhibitor [Yang, L, et al., (2007) Inhibition of epidermal growth factor receptor signaling elevates 15-hydroxyprostaglandin dehydrogenase in non-small-cell lung cancer. Cancer Res 67:5587-5593], 20 μM SB203580 (p38 MAPK inhibitor [Hsieh, Y H, et al., (2007) p38 mitogen-activated protein kinase pathway is involved in protein kinase Calpha-regulated invasion in human hepatocellular carcinoma cells. Cancer Res 67:4320-4327].

PCR or RT-PCR

The PCR or RT-PCR was performed following manufacturer's instructions.

Plasmid Constructs

The PTP4A3 DNA clone (Cat #: MHS1011-59590) provided by Openbiosystems (Huntsville, Ala.) was used as template and amplified by PCR with the primer pairs, 5'-atggctcg-gatgaaccgcccg-3' [SEQ ID NO: 4] and 5'ctacataacgcagcaccgggt-3' [SEQ ID NO: 5]. The in-frame DNA fragment of PTP4A3 (B0003105, amino acid 1-174) was then subcloned into the pcDNA3HA vector (Tang, et al., 2005) to generate a pcHAPTP expression vector. A series of PTP4A3 deletions (del) were constructed and numbered from 1-9 as follows: #1 del contained the amino acids (a.a 102-174) of PTP4A3 but added one methionine (M) for initiation. The DNA fragment generated by PCR with the primer pairs 5'-atggtgcactgcgtggcgggc-3' [SEQ ID NO: 6] and 5'-ctacataacgcagcaccgggt-3' [SEQ ID NO: 5] was inserted into the pcDNA3HA vector; #2 del contained the a.a. (55-174) but added one methionine (M) for initiation. The DNA fragment generated by PCR with the primer pairs 5'-atgaaaacgccgctg-gagaaggat-3' [SEQ ID NO: 7] and 5'-ctacataacgcagcaccgggt-3' [SEQ ID NO: 5] was inserted into the pcDNA3HA vector; #3 del contained the a.a. (39-174) but added one methionine (M) for initiation. The DNA fragment generated by PCR with the primer pairs 5'-atgaagtacggggctaccact-3' [SEQ ID NO: 8] and 5'-ctacataacgcagcaccgggt3' [SEQ ID NO:5] was inserted into the pcDNA3HA vector; #4 del contained the a.a. (1-145) but added one stop codon at end of ORF. The DNA fragment generated by PCR with the primer pairs 5'-atggctcggatgaac-cgcccg-3' [SEQ ID NO: 4] and 5'-ctactgcttgctgttgatggc-3' [SEQ ID NO: 9] was inserted into the pcDNA3HA vector; #5 del contained the a.a. (1-118) but added one stop codon at end of ORF. The DNA fragment generated by PCR with the primer pairs 5'-atggctcggatgaaccgcccg-3' [SEQ ID NO: 4] and 5'-ctaacagaacttggccttcac-3' [SEQ ID NO: 10] was inserted into the pcDNA3HA vector; #6 contained the a.a. (1-66) but added one stop codon at end of ORF. The DNA fragment generated by PCR with the primer pairs 5'-atggctcg-gatgaaccgcccg-3' [SEQ ID NO: 4] and 5'-ctacacaacggtgatgc-catc-3' [SEQ ID NO: 11] was inserted into the pcDNA3HA vector; #7 del contained the a.a. (1-38) but added one stop codon at end of ORF. The DNA fragment generated by PCR with the primer pairs 5'-atggctcggatgaaccgcccg-3' [SEQ ID NO: 4] and 5'-ctacttcaggtcctcaatgaa-3' [SEQ ID NO: 12] was inserted into the pcDNA3HA vector; #8 del contained the a.a. (55-69) but added one methionine (M) for initiation and one stop codon at end of ORF. The DNA fragment generated by PCR with the primer pairs 5'-atgaaaacgccgctggagaaggat3' [SEQ ID NO: 7] and 5'-ctagctcagccagtcttccac-3' [SEQ ID NO: 13] was inserted into the pcDNA3HA vector; #9 contained the a.a. (39-66) but added one methionine (M) for initiation and one stop codon at end of ORF. The DNA fragment generated by PCR with the primer pairs 5'-atgaagtacggggctaccact-3' [SEQ ID NO: 8] and 5'-ctacacaacggtgatgccatc-3' [SEQ ID NO: 11] was inserted into the pcDNA3HA vector.

RNA Interference (RNAi) of PTP4A3

THP-1 cells ($5\times10^6$) matured by treatment with 200 nM phorbol 12-myristate 13-acetate (Sigma) were treated or untreated with 0.1 µg/ml LPS (Sigma) for 3 h and washed with PBS. Cells were then transfected by Oligofectamine (Invitrogen) with 100 nM of small interfering RNA (siRNA) specific for PTP4A3 (named PTP4A3RNAi with duplex sequences: GUACGAGGACGCCAUCCAGUU [SEQ ID NO: 14] & AACUGGAUGGCGUCCUCGUAC [SEQ ID NO: 15], designed and synthesized by Invitrogen) and 100 nM of nonspecific siRNA (named NSRNAi, Tang, et al., 2005) as control following manufacturer's instructions. The treated or untreated cells were grown in RPMI medium 1640 with 10% FBS and maintained at 37° C. in 5% $CO_2$ overnight. The protein lysate from the treated or untreated cells were analyzed by Western blotting.

Peptides

Synthetic peptides were supplied by Biosynthesis, Inc. (Lewisville, Tex.). PIMAP39 consisted of the PTP4A3 sequence KYGATTVVRVCEVTYDKTPLEKDGITVV [SEQ ID NO: 1] located in the region from amino acids 39 to 66. SCpep served as a negative control peptide and consisted of the randomly scrambled sequence VTGKLTDTEVVTAYVIDEPKYVCRVTGK [SEQ ID NO: 16] (Medusa Random Sample Generator Software, Randombots.com). Both peptides were solubilized in DMSO immediately prior to use.

Fluorescence Microscopy

Fluorescein 5-isothiocyanate (FITC) labeled PIMAP39 was supplied by Biosynthesis, Inc (Louisville, Tex.). FITC-PIMAP39 was solubilized in DMSO and delivered into mouse macrophages or mouse circulatory system. For macrophage samples, cells ($5\times10^3$) from 3 month old mice were seeded over cover slips (22 mm, VWR Scientific) in 6 well plates at 37° c. and 5% $CO_2$ overnight. After washing by PBS, the cells were treated with 500 ng/ml FITC-PIMAP39 (B) or DMSO (A) as control. Cells were continuously incubated in RPMI 1640 supplemented with 10% FBS at 37° C. and 5% $CO_2$ overnight. The cover slips were removed from the wells and the attached cells were stained with 50 nM LysoTracker Red DND-99 (Invitrogen) for 1.5 hours and then air-dried. For tissue section samples, mice were treated with 1 mg of FITC-PIMAP39 (E&F) or DMSO (C&D) as control by tail vein injection as described [Sossey-Alaoui, K, et al., (2007) Down-regulation of WAVE3, a metastasis promoter gene, inhibits invasion and metastasis of breast cancer cells. Am J Pathol 170:2112-2121]. One hour post injection mice were sacrificed and their livers were immediately harvested. Harvested livers were set in uniform orientations in molds using Histoprep (Fisher). 10 µm thick cross-sections were cut and transferred with a paintbrush to glass slides followed by H&E (hematoxylin and eosin) staining.

Cryosections (of, e.g., cross-sectional views) were made at −24° c. using an HM505E cryostat (Microm; Waldorf, Germany). Both the treated cells and sections above were exposed to visible light and fluorescent light by Olympus BX40 microscope at 200× (A&B) or 1000× (C-F) magnification. The images were taken with MicroFIRE™ camera (Olympus, Center Valley, Pa.) under uniform exposure time (1 second for fluorescent light, 30 msec for visible light). The analysis of these images was performed using a program, Image-Pro™ plus 5.0 (MediaCybernetics, Bethesda, Md.).

IP-PTPs

Cultures of U2OS cells ($5\times10^6$) were transfected with PTP DNA constructs or pcDNA3 as control using Lipofectamine™ Reagent (Invitrogen; Carlsbad, Calif.) overnight in DMEM with 10% FBS at 37° C. and 5% $CO_2$. The proteins from the treated cells were extracted with lysis buffer (Promega; Madison, Wis.) plus a cocktail of protein inhibitors (Sigma, St. Louis, Mo.) following the manufacturer's instructions. The immunoprecipitation was done using a Protein A/G Plus-Agarose (sc-2003; Santa Cruz Biotechnology; Santa Cruz, Calif.) and an antibody to HA (sc-805, Santa Cruz Biotechnology) following the manufacturer's instructions. The 1 µg protein of each IP-PTP was confirmed by Western blot with HA antibody.

Western Blot Analysis

Cultures of U2OS cells ($1\times10^5$), THP-1 ($1\times10^5$) or mouse macrophage cells ($1\times10^5$) were transfected with DNAs by using Lipofectamine Reagent (Invitrogen) according to manufacturer's instructions. Cells were incubated in 6-well plates at 37° C. and 5% $CO_2$ overnight. The proteins from the treated cells or untreated controls were extracted with lysis buffer (Promega) plus a cocktail of protein inhibitors (Sigma) per the manufacturer's instructions and suspended in SDS sample buffer, then applied to SDS-polyacrylamide gels and detected by Western blotting. Antibodies were purchased from the following vendors: LITAF (611615, BD Biosciences, San Jose, Calif.), Actin (C-11, Santa Cruz Biotechnology, Santa Cruz, Calif.), Phosphotyrosine (610000, BD Transduction Labs, San Jose, Calif.), HA (sc—805), p38(sc-535), p-p38 (sc-7973), NF-κBp65 (sc-7151), p-NF-κBp65 (sc-33020-R), and p-Akt1/2/3 (sc-7985-R).

ELISA

For primary mouse macrophages or THP-1, cells were seeded ($2\times10^4$ cells in 96-well plate or $2\times10^6$ cells in six-well plate) and were stimulated with 0.1 pg/ml of E. coli LPS (Sigma) and/or transiently transfected with 1 pg of DNA using Lipofectamine™ Reagent and/or introduced with 500 ng/ml peptide using Chariot™ kit (ActiveMotif; Carlsbad, Calif.) prior to LPS treatment, then incubated at 37° C., 5% $CO_2$ overnight. Culture supernatants were harvested and centrifuged at 1,500×g to remove cell debris. Concentrations of mouse or human TNF-α in the supernatant of each well of treated and untreated control cells were measured by ELISA (Abraxis, Warminster, Pa.). ELISA immunoreactivity was quantified by using a microplate reader (Bio-Rad, Hercules, Calif.) and graphed.

Endotoxic Shock Assay

At the age of 8-12 weeks, weight-matched wild-type mice (n=15) weighing 20-25 g were injected intraperitoneal (i.p.) with lethal dose of LPS (12.5 ng LPS+1 mg D-Gal per gram body weight) followed immediately by tail vein injection of peptides or DMSO as control. The treated mice were maintained in a normal-light-cycle room and provided with free access to rodent chow and water and were monitored for their behavior and mortality every hour. The survival time of each treated mouse was recorded and a Kaplan-Meier graph was made based on the results. For blood plasma, blood was collected every 2 hours post injection for a total duration of 6 hours. To avoid causing death by blood loss, the duration of blood collection did not extend past 6 hours. Mice were warmed under heating lamp to promote blood flow, and a small incision was made on the tail. About 10-50 µl of blood was collected per animal at each time point (2, 4 or 6 hrs). The blood samples at each time point from mice within the same groups were pooled in order to have enough blood for ELISA.

Red blood cells were removed from the sample via centrifugation at 5×10³ rpm for 1 min using serum separator tubes (Fisher). Pooled plasma samples from each group were measured by ELISA (Abraxis; Warminster, Pa.) according to manufacturer's instructions. ELISA immunoreactivity was quantified by using a microplate reader (Bio-Rad, Hercules, Calif.) and the results from the 6 hr mark were graphed.

Results

LPS Signaling Cascade

To investigate a link between PTP4A3 and the LPS signaling cascade, HP-1 cells were co-treated with 0.1 µg/ml *E. coli* LPS and/or various inhibitors, sodium orthovanadate (PTP4A3 inhibitor), AG490 (JAK inhibitor), U0126 (ERK inhibitor), SB203580 (p38 MAPK inhibitor) or untreated as control. The supernatants from cell culture at each time point (2, 4, 6, 8, 10, 12, 14 and 16 hours post stimulation) were collected and the potential role of these inhibitors on TNF-α production was measured by ELISA (Abraxis; Los Angeles, Calif.). In parallel mRNA from each experimental group was prepared and quantified by RT-PCR. As shown by ELISA, with the exception of treatment with the inhibitor SB203580, all of the inhibitor treatments including, AG490 or U0126 or sodium orthovanadate did not result in a significant decrease in LPS-induced TNF-α expression compared to LPS alone. The result suggests a possible link between p38 activation and TNFα production by LPS. Interestingly, within 8-10 hrs post treatment, TNF-α levels in response to LPS alone, LPS+AG490, or LPS+U0126-treated cells did not increase at all, but later the levels rapidly increased compared to LPS+sodium orthovanadate-treated cells. Additionally, the concentration of secreted TNF-α by the LPS+sodium orthovanadate treated cells was on average 20% higher than LPS only treated cells at the 8 hr mark and beyond (FIG. 1A).

Figure 1C:
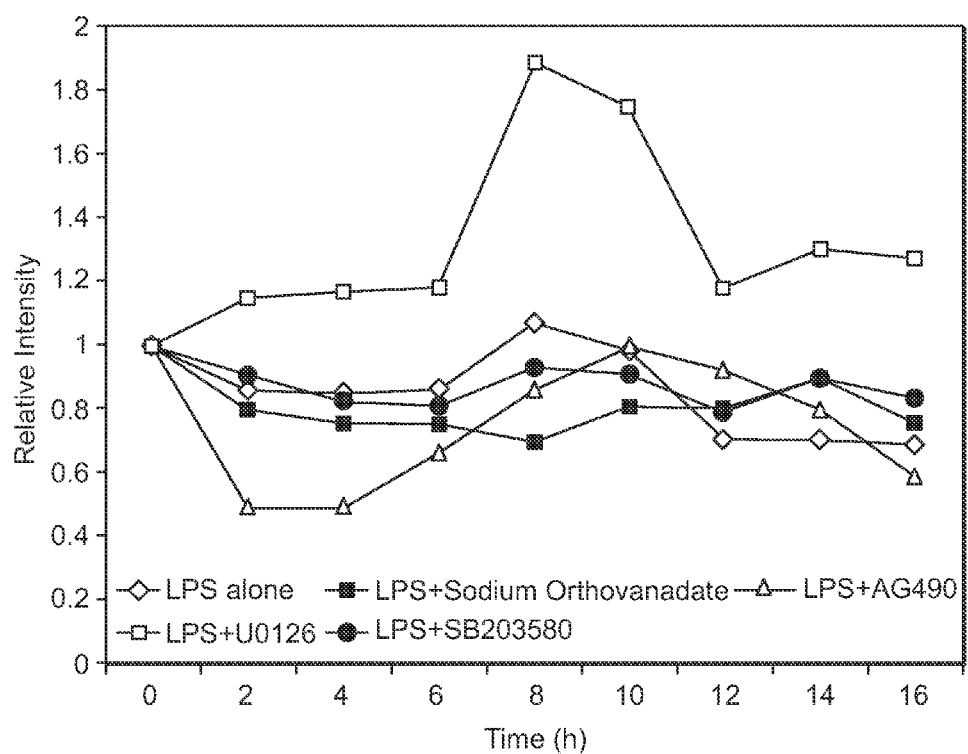

Curiously, RT-PCR analysis showed that PTP4A3 expression was at a maximum between 8-10 hrs post treatment with LPS alone or plus inhibitor, AG490 or U0126 or SB203580. No such maximum occurred with the LPS+sodium orthovanadate treated cells (FIGS. 1 B&C). This suggests that PTP4A3 is a LPS-induced short-lived protein regulating TNF-α levels and its expression is not affected by JAK or ERK or p38MAPK because inhibition of these kinases did not alter PTP4A3 gene expression in response to LPS.

LPS-Induces Tyrosine-Phosphorylation of PTP4A3 and its Derived Deletions

Figure 2:
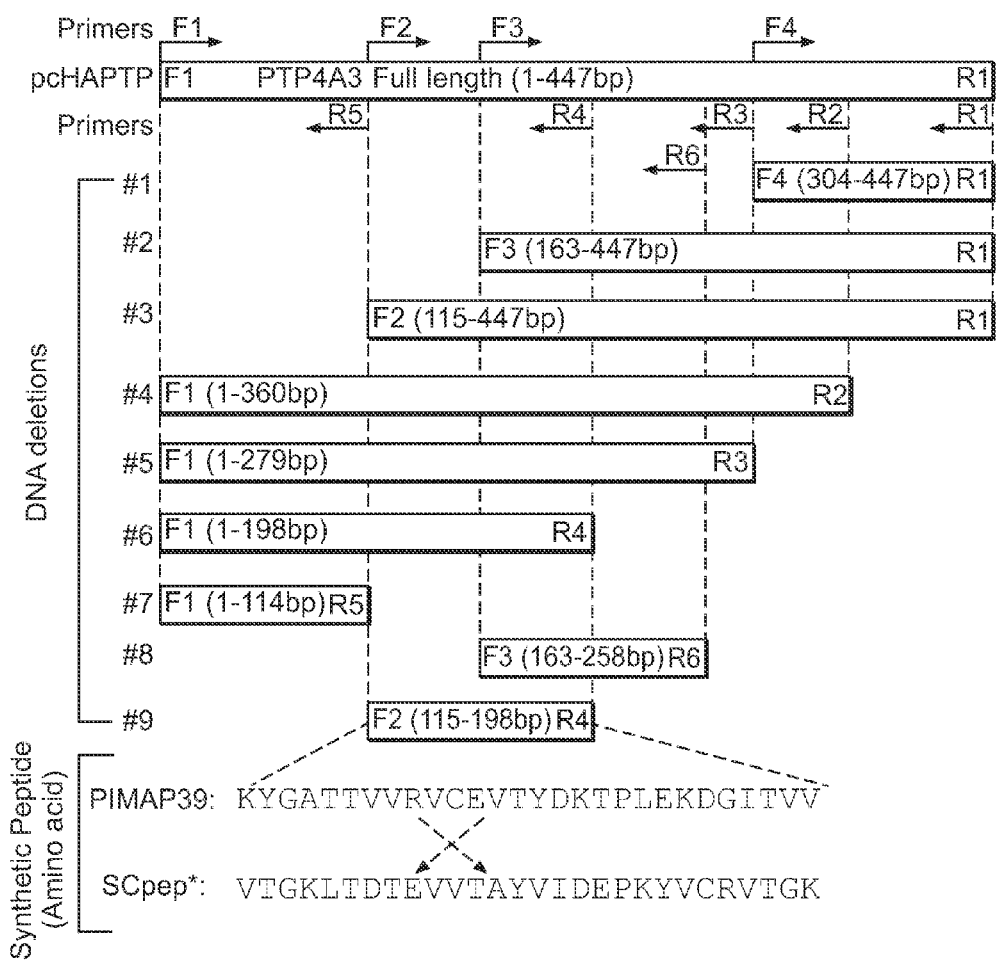
FIG. 2 shows a diagram of major PTP4A3 DNA constructs. Different lengths of PTP4A3 DNA were truncated and inserted into the pcDNA3HA vector (Tang, et al., 2005). Full length wild-type PTP4A3 (white box), named pcHAPTP and its derived segments (gray box, #1-19) are shown. The synthetic peptide representing amino acids 39 to 66, named PIMAP39 (SEQ ID NO: 1), and its randomly scrambled peptide as a negative control, named SCpep (SEQ ID NO: 16), are shown.

The treatment of cells with LPS induces PTP4A3 gene expression. Thus, it was contemplated that PTP4A3 will be consequently activated via tyrosine phosphorylation in response to LPS. To test this, a panel of truncated PTP4A3 was generated as presented in FIG. 2 in the following manner: (a.a. 1-149, full length, named pcHAPTP), #1 (a.a. 102-149), #2 (a.a. 55-149), #3 (a.a. 39-149), #4 (a.a. 1-120), #5 (a.a. 1-93) #6 (a.a. 1-66), #7 (a.a. 1-38), #8 (a.a. 55-86) and #9 (a.a. 39-66). Each of these constructs was individually transfected into LPS-untreated or treated mouse macrophage cells (1 µg/1×10⁵ cells) and then examined for tyrosine-phosphorylation. Western blot analysis of total cell lysates provided no clear evidence for tyrosine phosphorylation of PTP4A3 due to strong background as a result of numerous tyrosine phosphorylated proteins (FIGS. 3, A&D). Thus, these total cell lysates were subjected to immunoprecipitation (IP) using anti-HA antibody followed by western blot analysis using anti-phosphotyrosine antibody. The results (pcHAPTP, #2, #7 or #9) are shown here (FIGS. 3, B, C, E & F). The result shows that wild type PTP4A3 and the N-terminus truncated PTP4A3 (FIG. 2, #2) equally undergo tyrosine phosphorylation in response to LPS (FIG. 3F, lane 2-5). The constructs corresponding to N terminus (FIG. 2, #7) and central region of PTP4A3 (FIG. 2, #9) were also tyrosine phosphorylated in response to LPS, though their phosphorylation was slightly less than the wild type PTP4A3. All together, the data suggest that LPS induces tyrosine-phosphorylation of PTP4A3 in macrophage cells and the putative tyrosine phosphorylation sites are located in various region of PTP4A3.

Figure 4A:
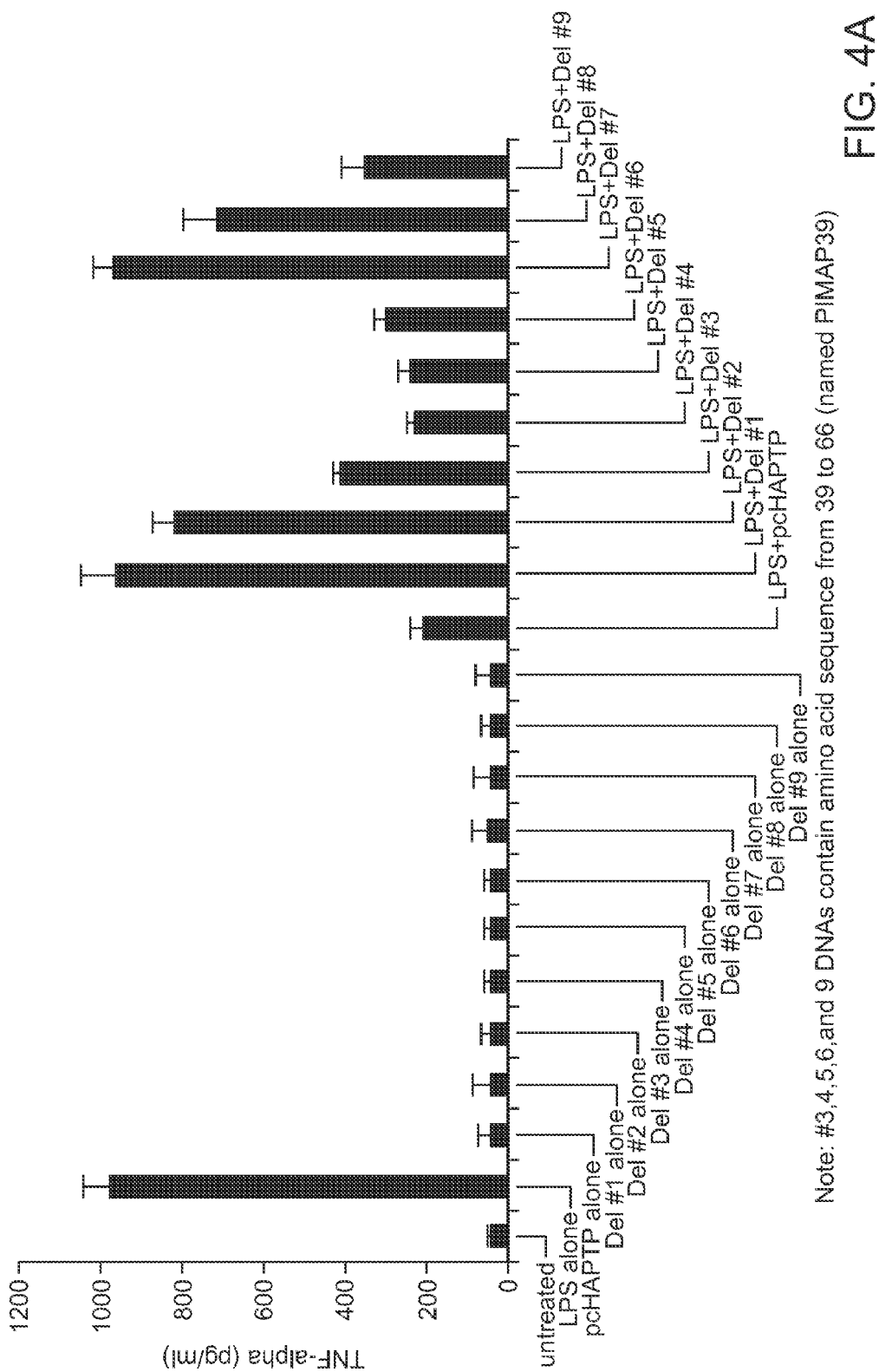
FIG. 4 shows the analysis of effects of transfected DNAs on LPS-induced TNF-α secretion and gene activation. THP-1 cells ($1 \times 10^5$) were stimulated with 0.1 µg/ml $E.$ $coli$ LPS for 3 hours. The cells were washed and transiently transfected with DNAs above using Lipofectamine™ reagent (Invetrogen). Treated cells were then incubated overnight. The supernatants from each culture were measured by ELISA. Elisa immunoreactivity was quantified using a microplate reader (Bio-Rad) and graphed (A). Multiple tests have been done with similar results. THP-1 cells (B) or mouse macrophage cells (C) were stimulated with 0.1 µg/ml $E.$ $coli$ LPS alone for 3 hours and then transfected with 1 µg/ml pcHAPTP DNA (B & C, lane 3) or 1 µg/ml pcDNA (B & C, lane 2) and untreated (B & C, lane 1) as controls by Lipofectamine reagent. Treated cells were incubated overnight and lysed. The lysate proteins were used for Western blot with antibodies against LITF (611614, BD Biosciences) and PRL-3 (sc-21581, Santa Cruz Biotechnology), p38 (sc-535), p-p38 (sc-7973). NF-κBp65 (sc-33020-R), p-Akt1/2/3 (sc-7985-R) and actin (sc-1615). For further analysis by RNA interference (RNA) of PTP4A3 (D), THP-1 cells were stimulated (D, lanes 2 & 3) or untreated (D, lanes 1, 4 & 5) with 0.1 µg/ml LPS (Sigma) then transfected by 0.5 mg pcHAPTP (D, lane 4 & 5) plus 100 nM PTP4A3RNAi (D, lane 3 & 5) or 100 nM nonspecific siRNA (NSRNAi) as control (D, lane 2 & 4) and incubated overnight. The protein lysates from treated and untreated cells were used for Western blot and antibodies against PRL-3, p38, p-p38 and actin.

Effects of Overexpression of PTP4A3 or its Derived Deletions on LPS-Induced TNF-α Production To investigate the possible involvement of PTP4A3 in LPS-induced TNF-α production in THP-1 cells these cells were treated with *E. coli* LPS and/or plus DNA constructs (FIG. 4A) and then assessed. The ELISA analysis showed that overexpression of these constructs significantly down-regulates LPS-induced TNF-α production provided they contained the a.a. 39-66 residue, such as with pcHAPTP (a.a. 1-149), #3 (a.a. 39-149), #4 (a.a. 1-120), #5 (a.a. 1-93), #6 (a.a. 166), and #9 (a.a. 39-66). Lacking this sequence (#1, a.a. 102-149; #7, a.a. 1-38) or containing only a partial residue (#2, a.a. 55-149; #8, a.a. 55-86) has failed to sufficiently down-regulate TNF-α production compared to controls. The same result was obtained in mouse macrophage cells (our unpublished data). The data suggest that the ability of PTP4A3 to regulate the LPS-induced TNF-α production requires the presence of this specific residue from a.a. 39-66.

Effects of PTP4A3 and its Derived Deletions on p38α/LITAF Signaling Pathway

Figures 4B, 4C, 4D:
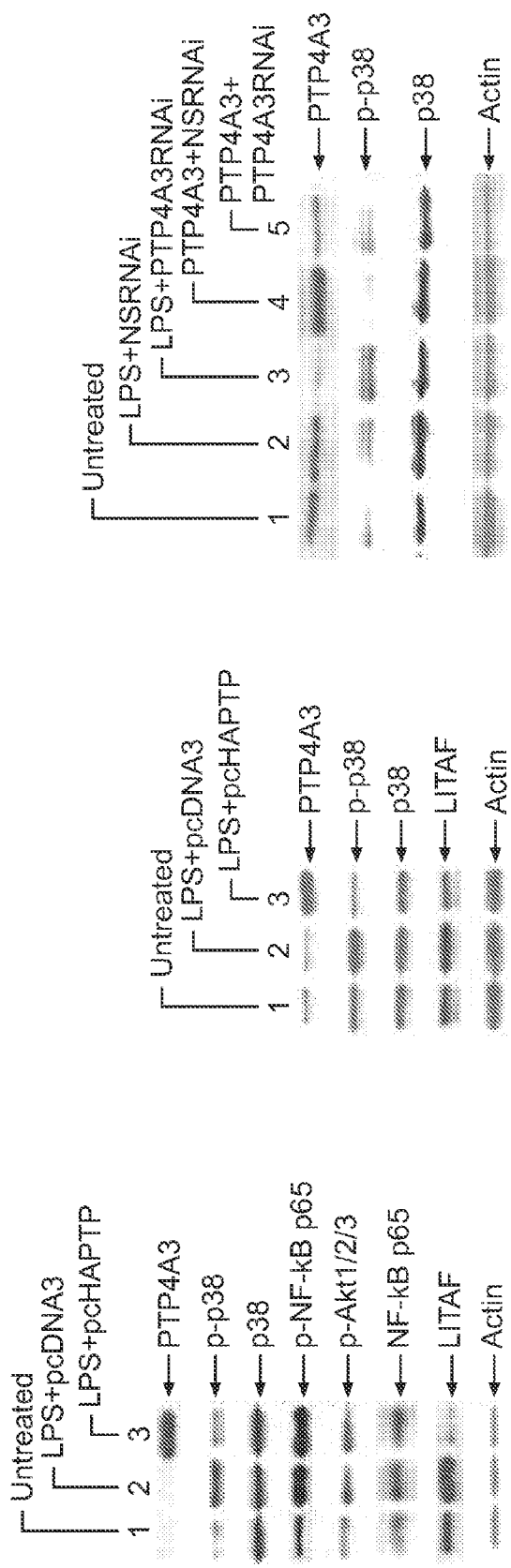
Figure 5A:
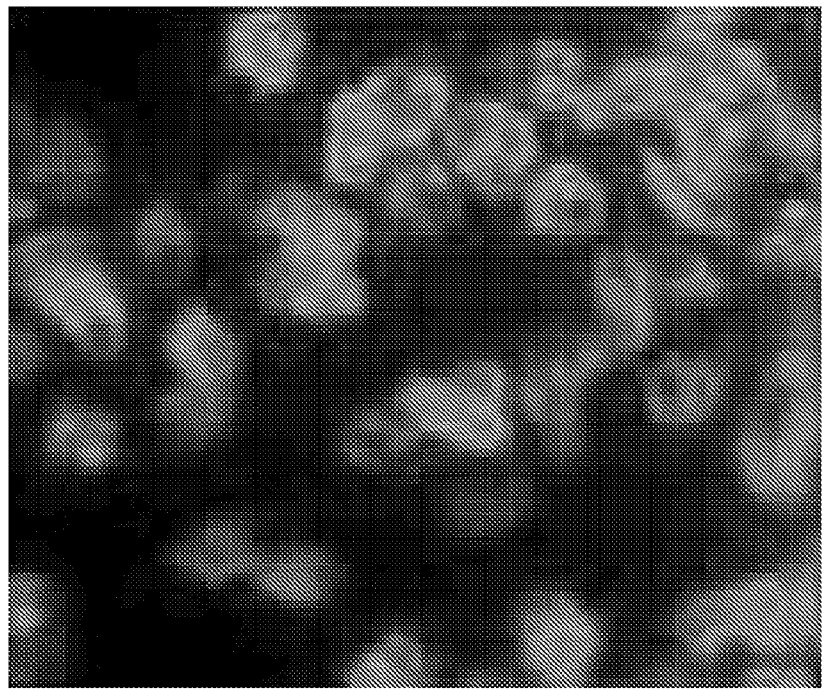
FIG. 5 shows detection of fluorescein 5-isothiocyanate (FITC)-labeled PIMAP39 in mouse macrophages (A & B) and mouse liver (sections C-F). Macrophage samples: Cells ($5 \times 10^3$) from 3 month old mice were seeded over cover slips (22 mm) in 6-well plates and were treated with 500 ng/ml FITC-PIMAP39 (B) or DMSO alone (A) and continuously incubated overnight. Cover slips were removed and cells were stained with 50 nM LysoTracker Red DND-99 (Invitrogen) for 1.5 hours and then air-dried. Tissue section samples: Mice were treated with 1 mg of FITC-PIMAP39 (E, F) or DMSO alone as control (C, D), by tail vein injection as described. One hour post injection mice were sacrificed and their livers were harvested. Harvested livers were set in uniform orientations in molds using Histoprep™ (Fisher). 10 µm thick cross-sections were cut and transferred with a paintbrush to glass slides followed by H & E staining. Cross-sections were made at −24° C. using an HM505E cryostat (Microm). Both the treated cells and sections above were exposed to visible light for structural identification (C & E) and fluorescent light for signal location (A, B, D & F) by Olympus BX40 microscope at 200× (A & B) or 1000× (C-F) magnification and photographed. The FITC-PIMAP39-induced fluorescent signal in some macrophages (B) or in the leukocytes within the veins of the liver (F) was observed. The images were taken with a MicroFIRE camera under exposure time (1 second for fluorescent light, 30 second for visible light). The data analysis was processed by the program, Image-Pro plus 5.0. Multiple tests have been performed with similar results. The results from one test were presented here.
Figure 5B:
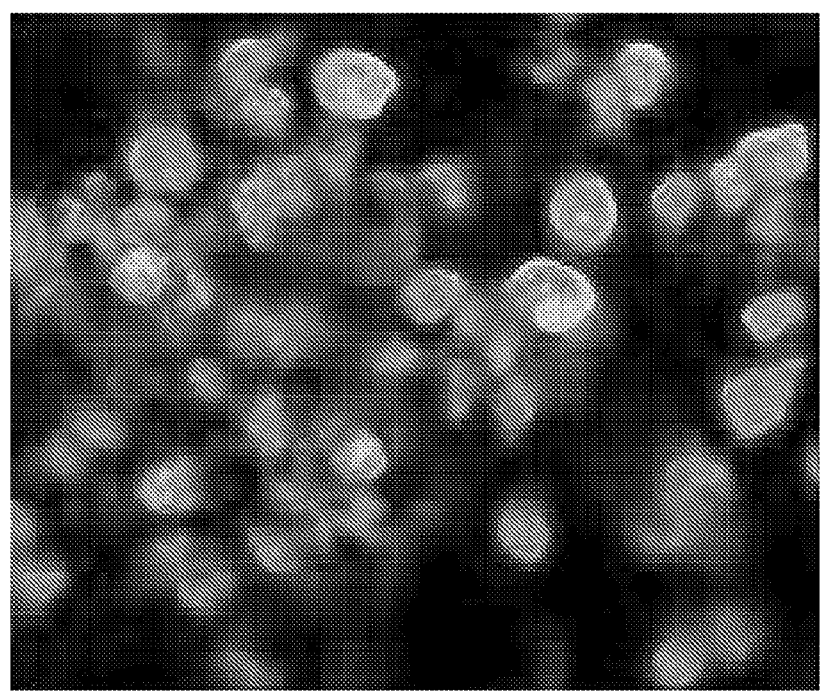
Figure 5C:
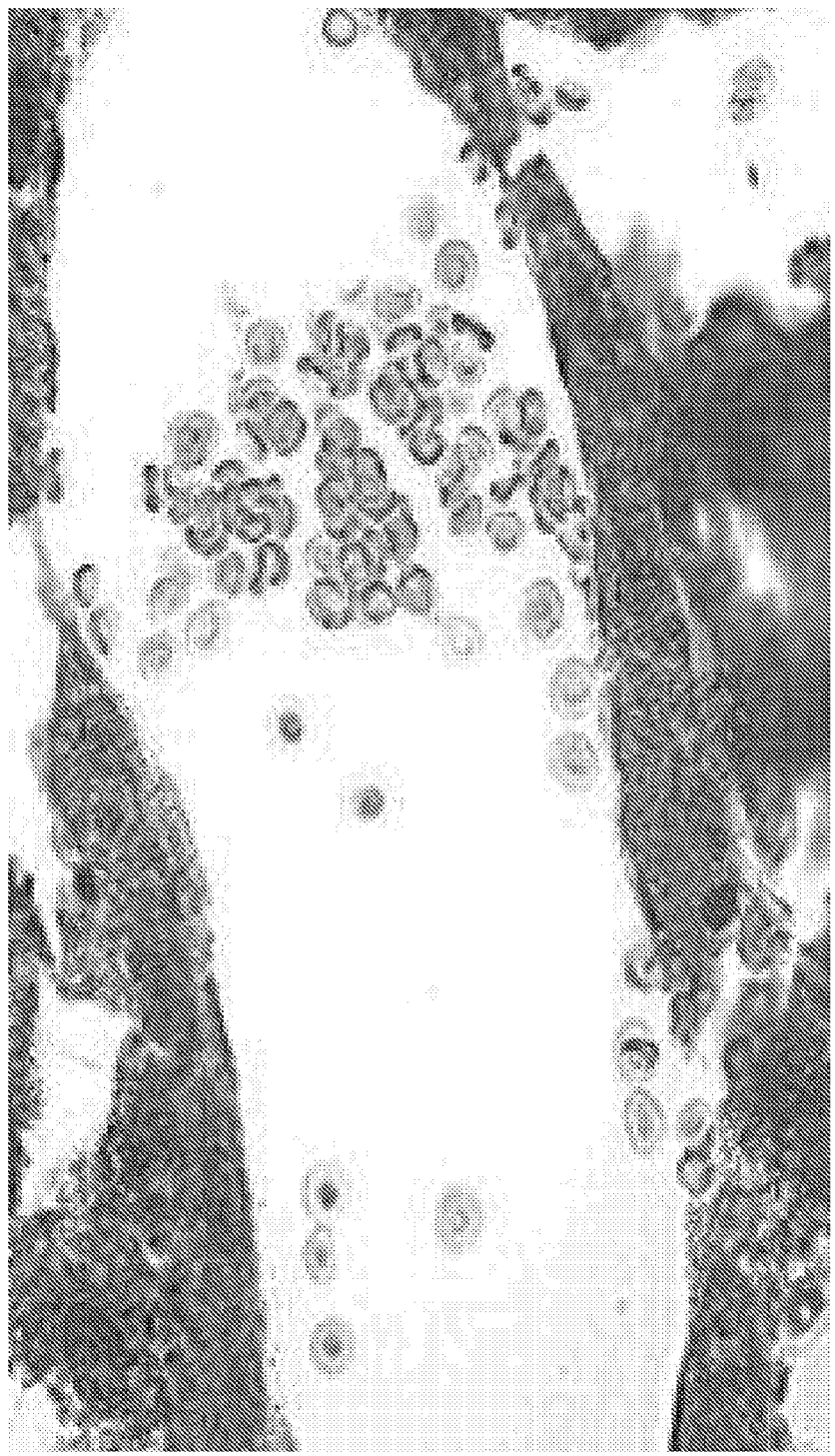
Figure 5D:
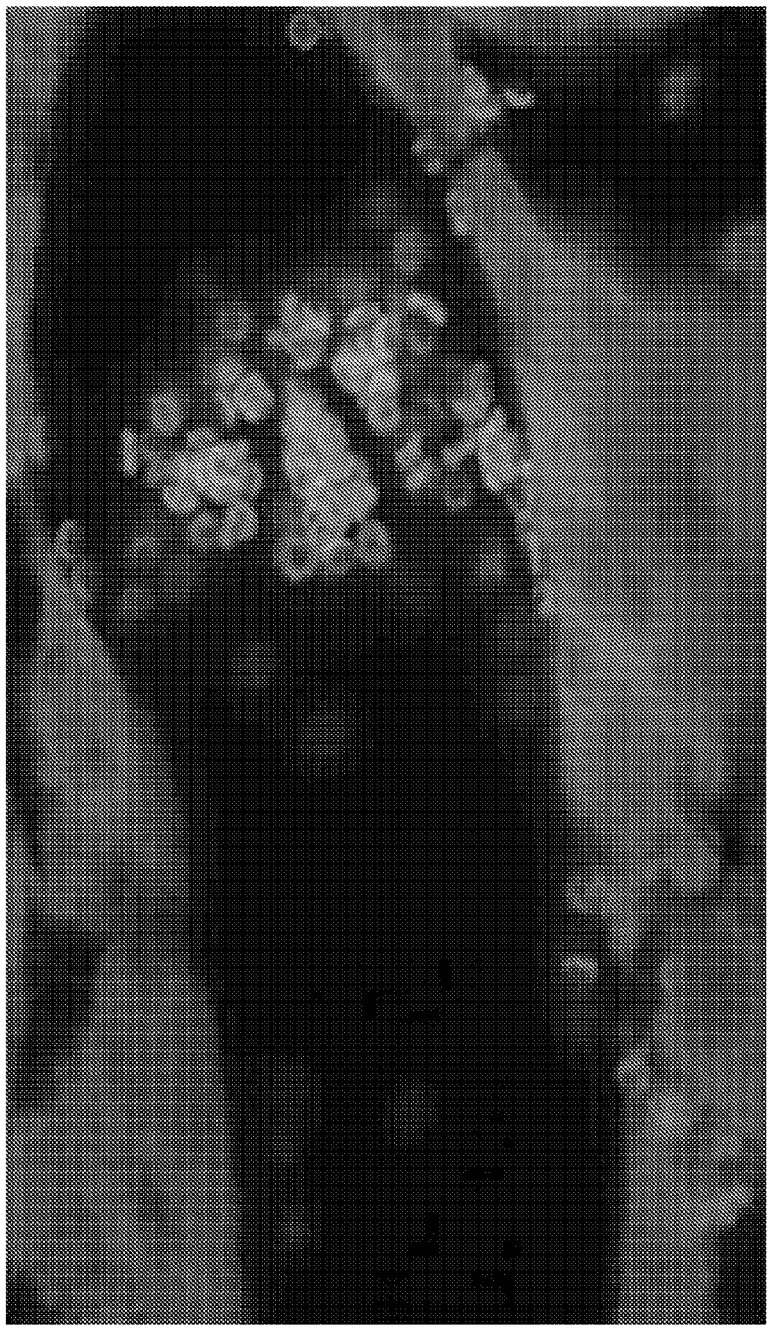
Figure 5E:
Figure 5F:
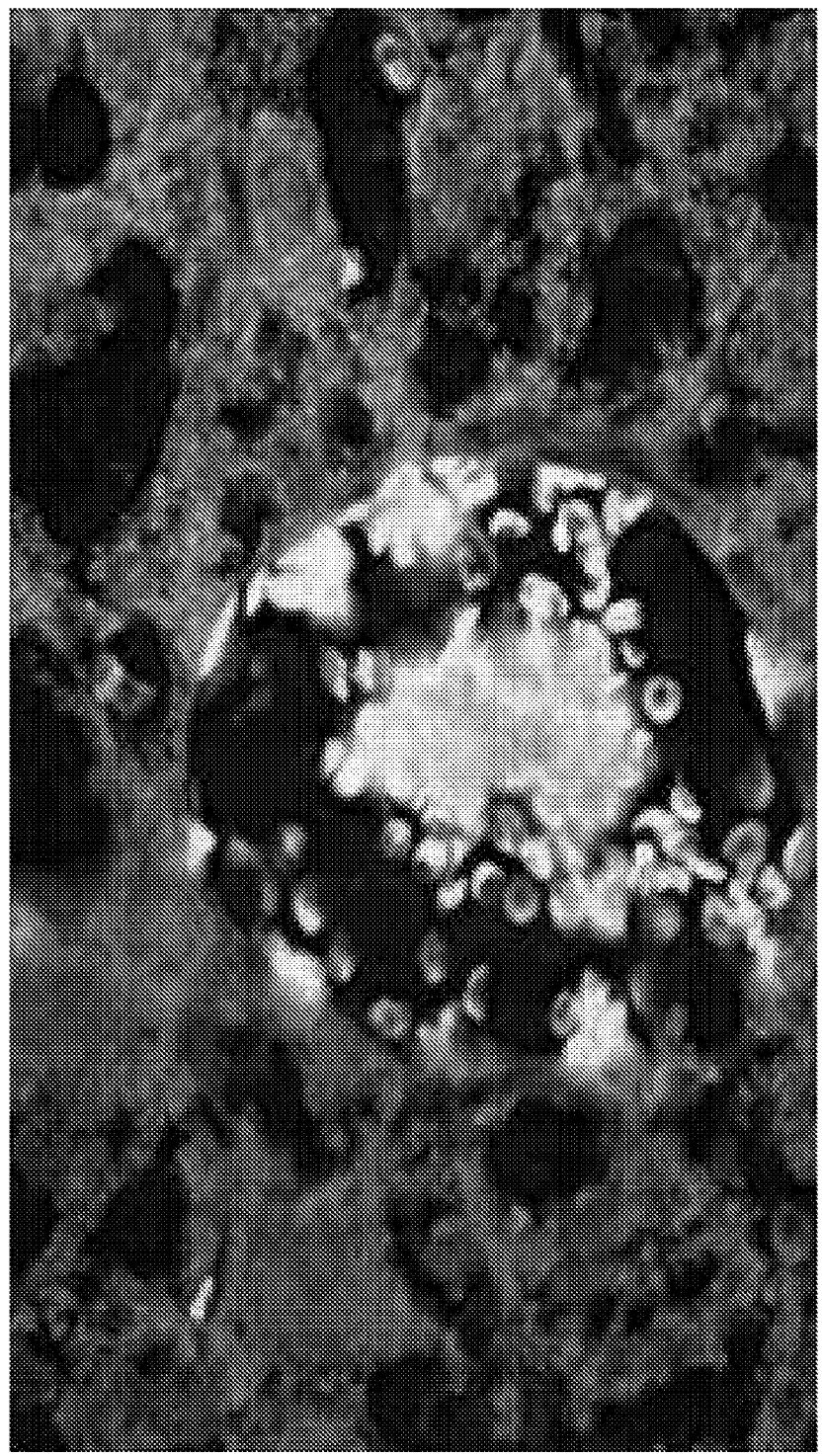

LITAF remains inactivated in the absence of p38 MAP kinase (p38α) and the inhibition of p38α down-regulates cytokines such as TNF-α [Tang, X, et al., (2006) LPS-induced TNF-alpha factor (LITAF)-deficient mice express reduced LPS-induced cytokine: Evidence for LITAF-dependent LPS signaling pathways. Proc Natl Acad Sci USA 103: 13777-13782]. Based on these findings, it was contemplated that PTP4A3 functions within this LPS-dependent p38α/LITAF signaling pathway. To test this hypothesis, THP-1 cells (FIG. 4B) were co-treated with *E. coli* LPS plus pcDNA3 DNA as control (FIG. 4B, lane 2) and PTP4A3 DNA (FIG. 4B, lane 3). The lysate protein from each treated cell culture was detected by Western blot analysis. As shown, overexpressing PTP4A3 (lane 3, HA detection) significantly reduced the p38α phosphorylation (lane 3, p-p38 detection) while at the same time unaffecting the p38α protein level (lane 3, p38 detection). Also, a reduction of LITAF was observed under the aforementioned conditions (lane 3, LITAF detection). Additionally, the PTP4A3 overexpression had no effect on both the protein and phosphorylation levels of NFκB (p65) and AKT 1/2/3 (lane 3) compared to the controls (lane 1 & 2). This suggests that PTP4A3 mediates dephosphorylation of p38α and consequently leads to the inhibition of LPS-induced LITAF production. The similar results in mouse macrophage cells are presented (FIG. 4C). To further characterize the role of endogenous PTP4A3 on p38α phosphorylation PTP4A3 expression was knocked-down using RNAi.

Silencing PTP4A3 expression significantly increased p38α phosphorylation in response to LPS (FIG. 4D, lane 3). Consistent with the role of PTP4A3 in p38α phosphorylation, overexpression of PTP4A3 reduced LPS-induced phosphorylation of p38α (4D, lane 4) while blocking PTP4A3 expression with RNAi suppressed its ability to dephosphorylate p38 (4D, lane 5), suggesting that in vivo, PTP4A3 is an endogenous regulator of p38 in response to LPS stimulation.

Effects of PIMAP39 on p38α/LITAF Signaling Pathway

Figures 6A, 6B:
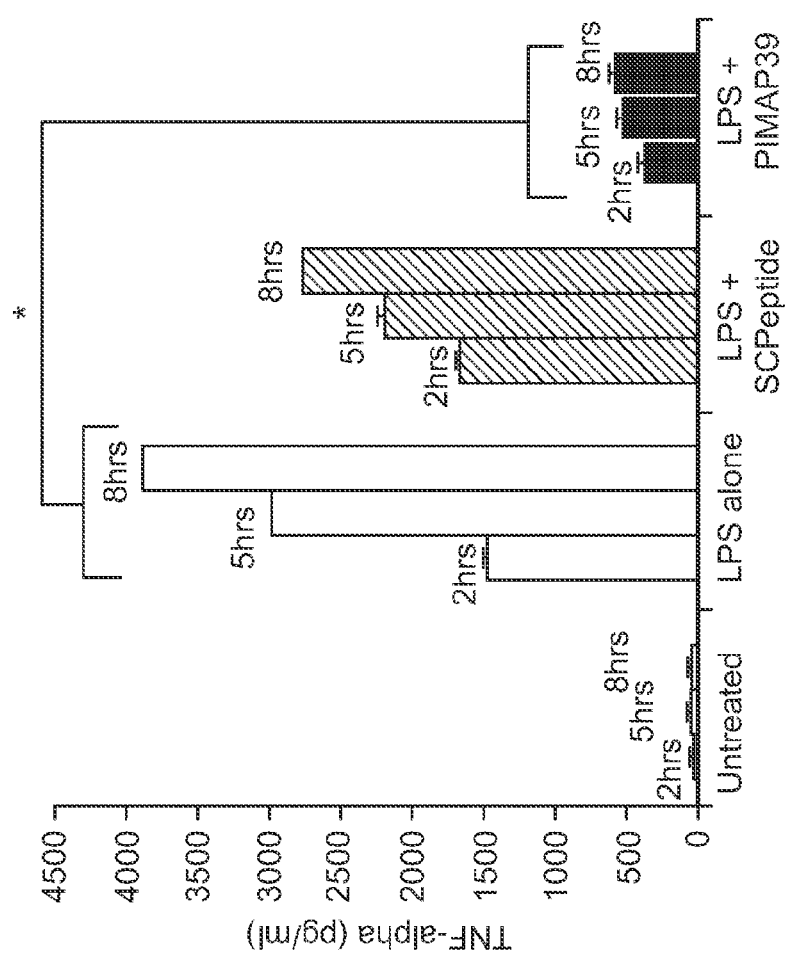
FIG. 6 shows a time course analysis of the effects of PIMAP39 on LPS-induced TNF-α secretion. PMA-pretreated THP-1 cells were seeded in 6-well plates ($1 \times 10^5$ cells) and stimulated with 0.1 mg/ml $E.$ $coli$ LPS for 3 hours. The cells were washed with PBS and given fresh medium prior to treatments with 500 ng/ml FITC-PIMAP39 (B) or SCpep (A) as control by Chariot kit (ActiveMotif, Carlsbad, Calif.) following manufacturer's instructions. 200 ml of supernatant was collected from each cell culture at each time point. (2, 5 and 8 hours) post treatment described above. The supernatants were measured by ELISA (Abraxis) to see effects of PIMAP39 on TNF-α production. ELISA immunoreactivity was quantified using a microplate reader (Bio-Rad) and graphed (A). Furthermore, cells were lysed in lysis reagent (Promega) and the lysate proteins were used for Western blot detection (B) with antibodies against LITAF (611614, BD Biosciences), p38 (sc-535, Santa Cruz Biotechnology, p-p38 (sc-7973) and actin (sc-1615). Multiple tests have been done with similar results. The results from one test are presented here.

A short peptide (named PIMAP39, FIG. 2) was synthesized with the amino acid sequence from a.a. 39 to 66 (KYG-ATTVVRVCEVTYDKTPLEKDGITVV [SEQ ID NO: 1]) of PTP4A3, the region which was found to function as an inhibitor of TNF-α production as described above (FIG. 4A). A FITC (fluorescein 5-isothiocyanate) tagged PIMAP39 was also synthesized in order to detect and establish that the peptide could be delivered into cells or the circulatory system. As shown in FIG. 5, FITC-labeled PIMAP39 delivered in macrophages or delivered by injection into mice was clearly present in both the treated macrophages (B) and the white blood cells within the liver sections (F) when observed with fluorescent light compared to the DMSO alone-treated (A&D). This suggests that the FITC-labeled PIMAP39 peptide entered the cells and tissues via circulating blood to produce the fluorescent signal both in vitro and in vivo. To further examine the effects of PIMAP39 on LPS-induced TNF-α production, a time course analysis was performed. THP-1 cells were treated with E. coli LPS plus PIMAP39 or SCpep as control. The supernatants from each cell culture at designated time points (2, 5 and 8 hrs post stimulation) were collected and measured by ELISA (FIG. 6A) and the corresponding lysate protein was detected by Western blot (FIG. 6B). It is clear that PIMAP39-treated cells secreted significantly less amount of TNF-α coinciding with a markedly lower level of both phosphorylated p38α and LITAF gene expression compared to the controls (FIG. 6A). This suggests that PIMAP39 is sufficient to dephosphorylate p38α consequently leading to the downregulation of LITAF (FIG. 6B, lane 5).

The Effect of PIMAP39 on In Vivo LPS-Induced Endotoxic Shock

Figure 7A:
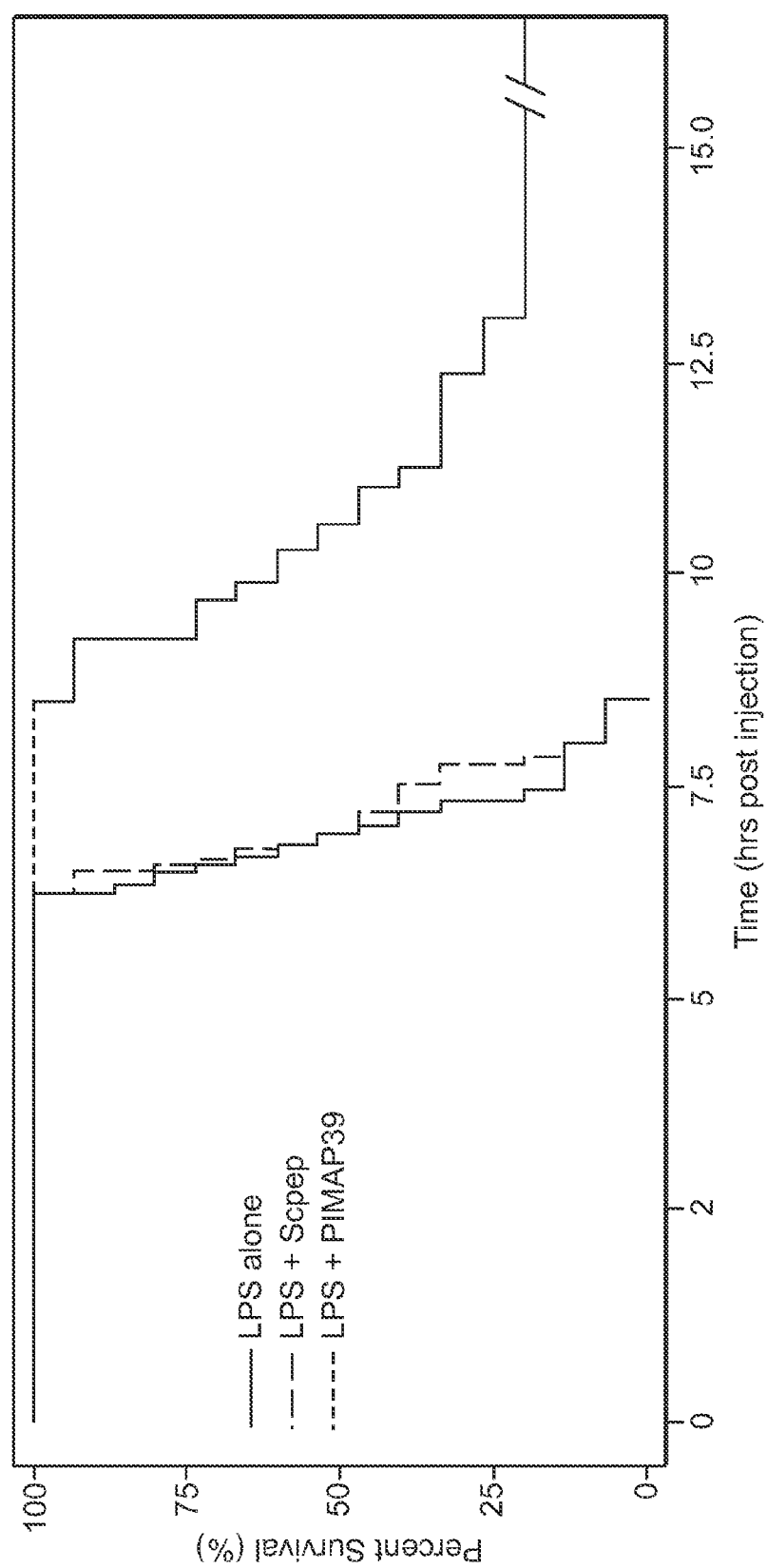
FIG. 7 shows an analysis of the effect of PIMAP39 on LPS-induced endotoxic shock. (A) Weight-matched wild-type mice (n=15) were injected intraperitoneal (i.p.) with a lethal dose of LPS (1 mg D-Gal+12.5 ng LPS per gram body weight) followed immediately by tail vein injection of DMSO (black line), 40 ug/g SCpep as control (green line) or 40 mg/g PIMAP39 (red line). The treated mice were monitored for their behavior and mortality every hour. The survival time of each treated mouse was graphed. Significant differences were noted between the PIMAP39 treated mice and both the LPS alone and LPS+SCpep groups (P<0.0001, log-rank and wilcoxon tests). (B) Blood was collected every 2 hours post injection for a total duration of 6 hours. Mice were warmed under heating lamps to promote blood flow and a small incision was made on the tail. About 10-50 µl of blood was collected per animal at each time point (2, 4 or 6 hours). Blood samples from mice within the same group were pooled. Red blood cells were removed from the sample via centrifugation at $5 \times 10^3$ rpm for 1 min using serum separator tubes (Fisher). Pooled plasma samples from the mice within each group were measured in triplets by ELISA (Abraxis) to see the effects of PIMAP39 on TNF-α production. ELISA immunoreactivity was quantitated using a microplate reader (Bio-Rad) and the results from the 6 hr mark were graphed (only the data for LPS+DMSO and LPS+PIMAP39 are presented here due to the similarity between LPS+DMSO and LPS+SCepetide).
Figure 7B:
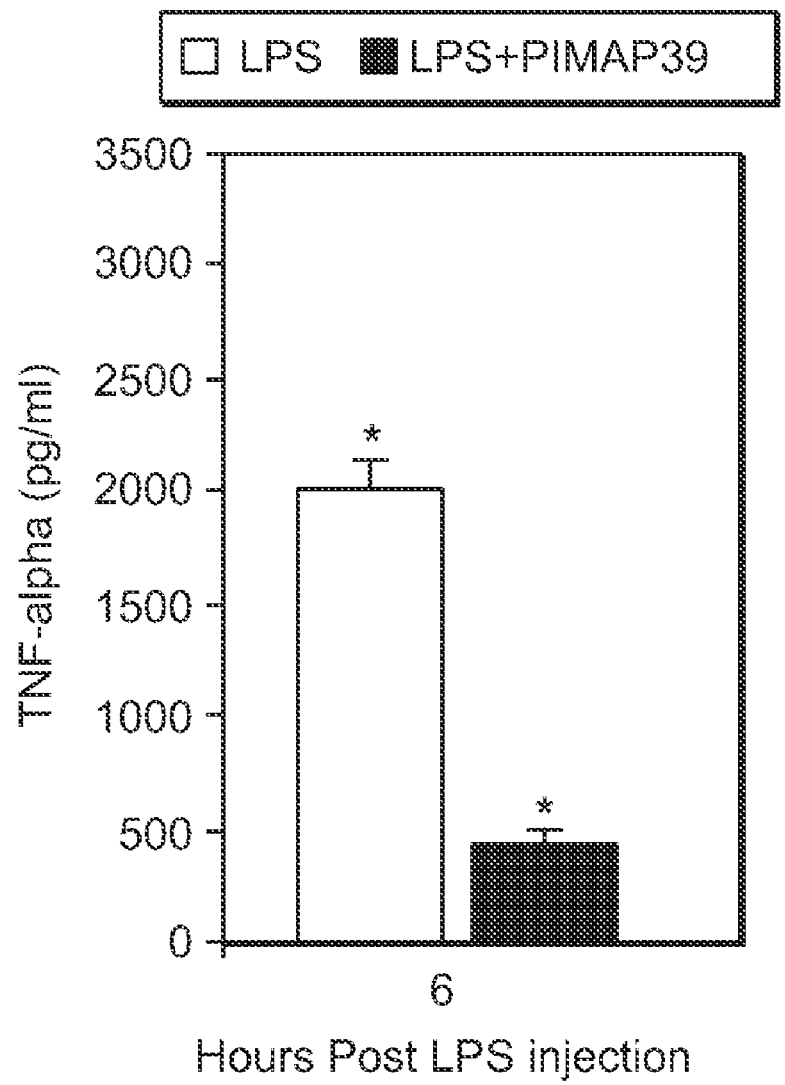

To investigate how PIMAP39 mediates endotoxic shock, 3 month old, weight matched mice were treated with a lethal dose of LPS (12.5 ng LPS+1 mg D-Gal per gram body weight) followed immediately by a tail vein injection of PIMAP39 or controls. The treated mice were monitored for their behavior and mortality every hour. The survival time of each treated mouse was measured and graphed (FIG. 7A). Most of the control mice (LPS+DMSO and LPS+SCpeptide) became sick at 3-4 hrs and deaths occurred between 6-8 hrs (FIG. 7A, black and green lines). Treatment with LPS plus 40 μg/g PIMAP39 (FIG. 7A, green line) delayed sickness and prolonged survival time by an average of 4 hours compared to the controls. Surprisingly, despite being administered a lethal dose of LPS, 3 of the PIMAP39 treated mice survived. Similar results were obtained when mice were treated with LPS plus a low concentration (0.4 μg/g) of PIMAP39 (our unpublished data). Furthermore, analysis of blood samples taken 2, 4 and 6 hrs post LPS treatment (FIG. 7B) showed that a rapid increase in TNF-α production occurred in control mice. However, under the same conditions, LPS+PIMAP39-treated mice maintained a 78.3% lower concentration of TNF-α compared to control mice.

This suggests that PIMAP39 provides treated mice with a significant resistance to LPS-induced endotoxic shock by inhibiting the subsequent rise in TNF-α post LPS injection.

What is claimed is:

1. A composition comprising an amino acid sequence consisting of SEQ ID NO: 1.

2. A composition comprising a nucleotide sequence encoding an amino acid sequence consisting of SEQ ID NO: 1.

3. An expression vector comprising a nucleotide sequence encoding an amino acid sequence consisting of SEQ ID NO: 1.

4. The composition of claim 1, additionally comprising a pharmaceutically acceptable carrier.

5. A method of reducing an LPS (lipopolysaccharide)-induced inflammatory response in a subject, the method comprising administering to the subject an effective amount of the composition of claim 1.

6. The method of claim 5, wherein said reduction in an LPS (lipopolysaccharide)-induced inflammatory response is detected by reduced levels of one or more of TNF-α and IL-1β.

* * * * *